United States Patent
Selvaraj et al.

(10) Patent No.: US 6,491,925 B2
(45) Date of Patent: *Dec. 10, 2002

(54) COMPOSITIONS AND METHODS FOR CANCER PROPHYLAXIS AND/OR TREATMENT

(75) Inventors: Periasmy Selvaraj, Tucker; Kenneth W. Sell, Atlanta, both of GA (US)

(73) Assignee: Emory University, Atlanta, GA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/929,464

(22) Filed: Aug. 15, 1997

(65) Prior Publication Data

US 2002/0009468 A1 Jan. 24, 2002

Related U.S. Application Data

(60) Provisional application No. 60/023,977, filed on Aug. 15, 1996.

(51) Int. Cl.[7] .................. A61K 39/00; A61K 45/00; C07H 21/02
(52) U.S. Cl. .................. 424/277.1; 424/278.1; 536/23.1
(58) Field of Search .................. 424/277.1, 278.1; 536/23.1

(56) References Cited

U.S. PATENT DOCUMENTS

| | | | |
|---|---|---|---|
| 5,223,394 A | 6/1993 | Wallner | 435/6 |
| 5,506,126 A | 4/1996 | Seed et al. | 435/172.3 |
| 5,767,077 A | * 6/1998 | Peltz et al. | 514/12 |

FOREIGN PATENT DOCUMENTS

| | | | |
|---|---|---|---|
| WO | WO95/03408 | 2/1995 | C12N/15/12 |

OTHER PUBLICATIONS

Roitt et al (Immunology, 1993, Mosby, St. Louis, see Glossary, p. 1.*
Azuma et al. "CD28 Interaction with B7 Costimulates Primary Allogeneic Proliferative Responses and Cytotoxicity Mediated by Small, Resting T Lymphocytes"; (1992) *J. Exp. Med.* 175:353–360.
Baskar et al. "MHC Class II–Transfected Tumor Cells Induce Long–Term Tumor–Specific Immunity in Autologous Mice"; (1994) *Cell Immunol.* 155(1):123–133.
Baskar et al. "Major histocompatibility Complex Class II[+]B7–1[+] tumor cells are potent vaccines for stimulating tumor rejection in tumor–bearing mice"; (1995) *J. Exp. Med.* 181:619–629.
Brian, A.A. "Stimulation of B–cell proliferation by membrane–associated molecules from activated T cells"; (1988) *Proc. Natl. Acad. Sci. USA* 85:564–568.
Brunschwig, E.B. "Glycosylphosphatidylinositol–modified murine B7–1 and B7–2 retain costimulator function"; (1995) *J. of Immunol.* 155:5498–5505.

Caras et al. "Signal for attachment of a phospholipid membrane anchor in decay accelerating factor"; (1987) *Science* 238:1280–1283.
Chen et al. "Costimulation of T cells for tumor immunity"; (1993) *Immunol. Today* 14:483–486.
Chen et al. "Rejection of K1735 murine melanoma in syngeneic hosts requires expression of MHC class I antigens and either class II antigens or IL–2[1]"; (1993) *J. Immunol.* 151:244–255.
Chen et al. "Costimulation of antitumor immunity by the B7 counterreceptor for the T lymphocyte molecules CD28 and CTLA–4"; (1992) *Cell* 71:1093–1102.
Chen et al. "B7–1/CD80–transduced tumor cells elicit better systemic immunity than wild–type tumor cells admixed with *corynebacterium parvum*"; (1994) *Cancer Res.* 54:5420–5423.
Chen et al. "Tumor immunogenicity determines the effect of B7 costimulation on T cell–mediated tumor immunity"; (1994) *J. Exp. Med.* 179:523–532.
Chouaib et al. "Interleukin 12 induces the differentiation of major histocompatibility complex class I–primed cytotoxic T–lymphocyte precursors into allospecific cytotoxic effectors"; (1994) *Proc. Natl. Acad. Sci. USA.* 91:12659–12663.
Damle et al. "Differential costimulatory effects of adhesion molecules B7, ICAM–1, LFA–3, and VCAM–1 on resting and antigen–primed CD4[+] T lymphocytes"; (1992) *J. Immunol.* 148:1985–1992.
Damle et al. "Costimulation via vascular cell adhesion molecule–1 induces in T cells increased responsiveness to the CD28 counter–receptor B7"; (1993) *Cell Immunol.* 148:144–156.
Damle et al. "Intracellular adhesion molecule–2, a second counter–receptor for CD11a/CD18 (leukocyte function–associated antigen–1), provides a costimulatory signal for T–cell receptor–initiated activation of human T cells"; (1992) *J. Immunol.* 148:665–671.
Fasel, N. et al. "In vitro attachment of glycosyl–inositol-phospholipid anchor structures to mouse Thy–1 antigen and human decay–accelerating factor"; (1989) *Proc. Natl. Acad. Sci. USA* 86:6858–6862.
Freeman et al. "B7, a new member of the Ig superfamily with unique expression on activated and neoplastic B cells"; (1989) *J. Immunol.* 143:2714–2722.

(List continued on next page.)

*Primary Examiner*—Susan Ungar
(74) *Attorney, Agent, or Firm*—Greenlee Winner and Sullivan PC

(57) ABSTRACT

Disclosed are compositions and methods to generate a protective or therapeutic immune response to neoplastic cells (e.g., tumor cells) which, in nature, lack a CoCAM surface molecule essential for a cytotoxic immune response. GPI-anchored CoCAM molecules are incorporated (by GPI-protein transfer) into neoplastic cells, neoplastic cell membrane preparations or neoplastic membrane vesicle preparations and formulated in immunogenic compositions. A specifically exemplified GPI-CoCAM is a B7.1/CD16B fusion protein, having the GPI anchor domain from the CD16B molecule.

3 Claims, 21 Drawing Sheets

OTHER PUBLICATIONS

Gajeweski et al. "Costimulation with B7–1, IL–6, and IL–12 is sufficient for primary generation of murine antitumor cytolytic T lymphocytes in vitro"; (1995) J. Immunol. 154:5637–5648.

Guo, Y. et al. "Effective tumor vaccine generated by fusion of hepatoma cell with activated B cells"; (1994) Science 263:518–520.

Hodgkin et al. "Separation of events mediating B cell proliferation and Ig production by using t cell membranes and lymphokines"; (1990) J. Immunol. 145:2025–2034.

Hodgkin et al. "Membranes from both Th1 and Th2 cell clones stimulate B cell proliferation and prepare B cells for lymphokine–induced differentiation to secrete Ig"; (1991) J. Immunol. 147:3696–3702.

Hollander et al. "Biosynthesis and function of LFA–3 in human mutant cells deficient in phosphatidylinositol–anchored proteins"; (1988) J. Immunol. 141:4283–4290.

Huang et al. "Protein transfer of preformed MHC–peptide complexes sensitizes target cells to T cell cytolysis"; (1994) Immunity 1:607–613.

Johnson and Jenkins "Accessory cell–derived signals required for T cell activation"; (1993) Immunol. Res. 12:48–64.

Kubin et al. "Interleukin 12 synergizes with B7/CD28 interaction in inducing efficient proliferation and cytokine production of human T cells"; (1994) J. Exp. Med. 180:211–222.

Kurosaki and Ravetch "A single amino acid in the glycosyl phosphatidylinositol attachment domain determines the membranes topology of FCγRIII"; (1989) Nature 342:805–807.

Lanier et al. "Membrane anchoring of a human IgG Fc receptor (CD16) determined by a single amino acid"; (1989) Science 246:1611–1613.

Lanier, L. "Distribution and function of lymphocyte surface antigens"; (1993) Ann. NY Acad. Sci. 677:86–93.

Li et al. "Costimulation of tumor–reactive $CD4^{30}$ and $CD8^+$ T lymphocytes by B7, a natural ligand for CD28, can be used to treat established mouse melanoma"; (1994) J. Immunol. 153:421–428.

Linsley et al. "Binding to the B cell activation antigen B7 to CD28 costimulates T cell proliferation and interleukin 2 mRNA accumulation"; (1991) J. Exp. Med. 173:721–730.

Linsley et al. "T–cell antigen CD28 mediates adhesion with B cells by interacting with activation antigen B7/BB–1"; (1990) Proc. Natl. Acad. Sci. USA 87:5031–5035.

Liu et al. "Co–stimulation of murine CD4 T cell growth"; (1992), Eur. J. Immunol. 22:2855–2859.

Liu et al. "Heat–stable antigen is a costimulatory molecule for CD4 cell growth"; (1992) J. Exp. Med. 175:437–445.

Low, M.G. "The glycosyl–phosphatidylinositol anchor of membrane proteins"; (1989) Biochem. Biophys. Acta 988:427–454.

Mackey et al. "Protective immunity induced by tumor vaccines requires interaction between CD40 and its ligand, $CD154^1$"; (1997) Cancer Res. 57:2569–2574.

McHugh et al. "Construction, purification, and functional incorporation on tumor cells of glycolipid–anchored human B7–1 (CD80)"; (1995) Proc. Natl. Acad. Sci. USA 92:8059–8063.

Murphy et al. "B7 and interleukin 12 cooperate for proliferation and interferon γ production by mouse T helper clones that are unresponsive to B7 costimulation"; (1994) J. Exp. Med. 180:223–231.

Nagarajan et al. "Reconstitution of CD16 expression on nucleated cells using purified CD16"; (1991) FASEB J. 5:A1718.

Nagarajan et al. "Purification and optimization of functional reconstitution on the surface of leukemic cell lines of GPI–anchored Fcγ receptor III"; (1995) J. Immunol. Meth. 184(2):241–251.

Noelle et al. "Cognate interactions between helper T cells and B cells"; (1991) J. Immunol. 146:1118–1124.

Noguchi et al. "Influence of interleukin 12 on p53 peptide vaccination against established Meth A sarcoma"; (1995) Proc. Natl. Acad. Sci. USA 92:2219–2223.

Parra et al. "Costimulation of human $CD4^+$ T lymphocytes with B7 and lymphocyte function–associated antigen–3 results in distinct cell activation profiles"; (1994) J. Immunol. 153:2479–2487.

Schwartz, R.H. "Costimulation of T lymphocytes the role of CD28, CTLA–4, and B7/BB1 in interleukin–2 production and immunotherapy"; (1992) Cell 1065–1068.

Selvaraj et al. "The major Fc receptor in blood has a phosphatidylinositol anchor and is deficient in paroxysmal nocturnal haemoglobinuria"; (1988) Nature 333:565–567.

Staunton et al. "Internalization of a major group human rhinovirus does not require cytoplasmic or transmembrane domains of $ICAM-1^1$"; (1992) J. Immunol. 148:3271–3274.

Townsend et al. "Tumor rejection after direct costimulation of $CD8^+$ T cells by B7–Transfected melanoma cells"; (1993) Science 259:368–370.

Townsend et al. "Specificity and longevity of antitumor immune responses induced by B7–transfected tumors"; (1994) Cancer Res. 54:6477–6483.

Tykocinski et al. "Glycolipid reanchoring of T–lymphocyte surface antigen CD8 using the 3' end sequence of decayaccelerating factor's mRNA"; (1988) Proc. Natl. Acad. Sci. USA. 85:3555–3559.

van Seventer et al. "Analysis of T cell stimulation by superantigen plus major histocompatability complex class II molecules or by CD3 monoclonal antibody: Costimulation by purfied adhesion ligands VCAM–1, ICAM–1, but not ELAM–1"; (1991) J. Exp. Med. 174:901–913.

Waneck et al. "Conversion of a PI–anchored protein to an integral membrane protein by a single amino acid mutation"; (1988) Science 241:697–699.

Waneck et al. "Molecular mapping of signals in the Qa–2 antigen required for attachment of the phosphatidylinositol membrane anchor"; (1988) Proc. Natl. Acad. Sci. USA. 85:577–581.

Wang et al. "Expression of heat–stable antigen on tumor cells provides co–stimulation for tumor–specific T cell proliferation and cytotoxicity in mice"; (1995) *Eur. J. Immunol.* 25:1163–1167.

Wettstein et al. "Expression of a class II Major histocompatibility complex (MHC) heterodimer in a lipid–linked form with enhanced peptide/soluble MHC complex formation at low pH"; (1991) *J. Exp. Med.* 174:219–228.

Yang et al. "Antitumor immunity elicited by tumor cells transfected with B7–2, a second ligand for CD28/CTLA–4 costimulatory molecules"; (1995) *J. Immunol.* 154:2794–2800.

Zhang, F. et al. "Spontaneous incorporation of the glycosyl–phosphatidylinositol linked protein Thy–1 into cell membranes"; (1992) *Cell Biology* 89:5231–5235.

McHugh et al. (1995) "Construction, Purification, and Functional Reconstitution on Tumor Cells of a Glycolipid Anchored B7–1 Molecule: a Novel Alternative to Gene Transfection in Human Immunotherapy" *Proceedings of The American Association ofor Cancer Research* Abstract. vol. 38. p. 494.

* cited by examiner

HLA CLASS I

HLA CLASS II

B7

GPI-B7 AFTER
PROTEIN TRANSFER

COMPOSITIONS AND METHODS FOR CANCER PROPHYLAXIS AND/OR TREATMENT

CROSS REFERENCE TO RELATED APPLICATIONS

This application is a Continuation-in-Part of U.S. Provisional Patent Application No. 60/023,977, filed Aug. 15, 1996. This application claims benefit of U.S. Provisional Application No. 60/023,977, filed Aug. 15, 1996.

ACKNOWLEDGEMENT OF FEDERAL RESEARCH SUPPORT

This invention was made, at least in part, with funding from the National Institutes of Health. Accordingly, the United States Government may have certain rights in this invention.

BACKGROUND OF THE INVENTION

The field of the present invention is in the area of immunotherapy, especially as it relates to the treatment and/or prophylaxis of cancer and/or tumors and compositions therefore.

The antitumor response is a very effective mechanism for eliminating tumors from the body. T cells play a major role in this elimination. To activate tumor-specific T cells, an initial signal need to be delivered by a T cell receptor interacting with the antigen-major histocompatibility complex (MHC) complexes expressed on antigen presenting cells (APC) (FIG. 1). The second signal is provided by costimulatory cell adhesion molecules (CoCAMS) present on the T cells interacting with their counter-receptors expressed on the APCs [Norton et al. (1992) J. Immunol. 149:1556–1561; Linsley et al. (1991) J. Exp. Med. 173:721–730; Azuma et al. (1992) J. Exp. Med. 175:353–360; June et al. (1994) Immunol. Today 15:321–331; Galvin et al. (1992) J. Immunol. 149:3802–3808]. When both signals are delivered, a normal T cell immune response occurs. The T cells expand, proliferate and develop into antigen-specific cytotoxic T lymphocytes (CTLs).

Tumor cells may also function as APC. These tumor cells, expressing an MHC-antigen complex and costimulatory adhesion molecules, can provide the necessary signals for the generation of tumor-specific CTLs. (FIG. 1). However, in the absence of the second signal from the tumor cells, tumor-specific T cells die [Tan et al. (1993) J. Exp. Med. 177:165–173; Gimmi et al. (1993) Proc. Natl. Acad. Sci. USA 90:6586–6590; Harding et al. (1992) Nature 356:607]. Tumors, by down-modulating cell adhesion molecules, can escape immune attack. Thus, by not providing the second signal the tumors not only avoid the immune system but also can, in effect, kill the T cells that are specific for the tumors [Townsend et al. (1993) Science 259:368–370; Li et al. (1994) J. Immunol. 153:421–428; Chen et al. (1994) J. Exp. Med. 179:532—532; Chen et al. (1992) Cell 71:1092–1102].

There are many CoCAMs important in development of the tumor-specific immune response. The most important receptor-ligand pairs in the immune system are interactions between CD2 and LFA-3, CD11 and ICAM-1, and CD28 with B-7.1 or B-7.2 [Johnson and Jenkins (1993) Immunol. Res. 12:48–64; Chen et al. (1993) Immunol. Today 14:483–486; Schwartz, R. H. (1992) Cell 1065–1068; Lanier, L. (1993) Ann. NY Acad. Sci. 677:86–93]. ICAMs are intercellular adhesion molecules. Among these three pairs, the CD28/CB7 interaction appears to provide the most important second signal for tumor-specific immunity [Townsend et al. (1993) supra; Li et al. (1994) supra; Chen et al. (1994) supra; Chen et al. (1992) supra].

Recently, CoCAMs, such as B7-1 and ICAM-1 [Chen et al. (1993) J. Immunol. 151:244–255], were expressed on tumor cells by gene transfer. These modified tumor cells did not grow in syngeneic mice, and also induced immunity against the parental tumor cell. This costimulation provided by the tumor cell is only necessary at the onset of the immune response. Once this is initiated, CTLs do not need CD28/B7 interaction to kill the target cell. Therefore, one can modify a tumor cell with B7-1 and stimulate the immune system to attack the unmodified tumor cell. Thus, modified tumor cells can be used as cancer vaccines.

Recently, Guo et al. [Guo et al. (1994) Science 265, 518–520] used another approach to prepare tumor vaccines. They generated tumor hybridomas by fusing hepatoma cells with activated B cells. These hybridomas expressed the tumor antigens as well as all the CoCAMs from the B cell. This hybridoma was able to immunize mice against the hepatoma.

There is a longfelt need in the art for compositions and methods effective in neoplasia, tumor and/or cancer prophylaxis and immunotherapy and a need for methods for making same without the introduction of cells carrying recombinant DNA into the vaccine preparations. The alternative methodology which the present invention uses is protein transfer.

SUMMARY OF THE INVENTION

It is an object of the present invention to provide compositions useful in immunotherapy, especially for the prophylaxis or treatment of neoplastic conditions and/or tumors, including cancer, for example, those tumors or cancers in which the cell membranes lack the CoCAM surface molecules including, but not limited to the B7-1 protein. The B7-1 protein is involved in costimulation of cells of the immune system via interaction with the CD28 protein of T cells.

Specifically exemplified compositions include those which comprise a fusion protein consisting of the extracellular, CD28 binding domain of B7-1 in combination with a glycosylated phosphatidylinositol (GPI) anchor domain, which GPI anchor domain is from membrane proteins including, but not limited to, decay accelerating factor, CD16, CD16B, and (preferably) LFA-3. As used herein, B7-1 is used synonymously with CD80. A specifically exemplified fusion protein consists of amino acids 1–243 of the B7-1 protein covalently joined to amino acids 193–234 of CD16B (See Freeman et al. (1989) infra, incorporated by reference herein). Other CoCAMs which can be modified to contain a GPI anchor include B7.2, ICAM-1, ICAM-2, VCAM-1 and LFA-3.

It is a further object of the invention to provide methods for incorporating the fusion protein(s) of the present invention into tumor cell membranes which in nature lack a CoCAM protein, such as the B-7.1 protein. The naturally occurring neoplastic cells or naturally occurring neoplastic cell membranes are prepared using art-known techniques, and then the fusion protein is added under conditions which allow the fusion protein to become embedded in the tumor cell membranes via a GPI anchor portion.

It is a further object of the invention to provide immunotherapeutic compositions comprising the neoplastic cells or neoplastic cell membranes (as isolated membranes or as intact or irradiated cells) into which the GPI-CoCAM fusion protein of the present invention has been embedded in combination with a pharmaceutically acceptable vehicle. Optionally, the immunotherapeutic composition can further include an immunological adjuvant which will enhance the cytotoxic immune response of an animal, including, but not limited to, a human, to which the composition is administered. Administration of the immunotherapeutic composition occurs by a route suitable for stimulating an immune response, and in particular, for activating a cellular immune response. Alternatively, the B7-1/CD16 fusion protein can be incorporated within the tumor cell membranes before the step of membrane purification (the fusion protein can be introduced into intact tumor cells) and preferably after homogenization of the tumor tissue to maximize cell membrane surface area available for embedding of B7-1/GPI fusion protein. Optionally, the immunotherapeutic compositions of the present invention can further include additional GPI-anchored fusion proteins which augment the costimulatory effect of the anchored B7-1 or other CoCAM protein. Further or in the alternative, these compositions of the present invention can additionally include at least one cytokine in an amount effective for the augmentation of the cytotoxic immune response. For this purpose, particularly preferred cytokines include, without limitation, interleukin-12 (IL-12) and interleukin-6 (IL-6).

Within the scope of the present invention are methods for the treatment of tumors and certain other neoplastic conditions, where these methods include the step of administering the immunotherapeutic composition comprising the B7-1/GPI or other GPI-CoCAM fusion protein, preferably the composition further includes an antigen suitable for stimulating cellular immunity and activating a cytotoxic response, as is well understood in the art, to an animal, including but not limited to, a human, where that animal has or has had at least one tumor having at least one marker surface antigen in common with those tumor cells used in the preparation of the immunotherapeutic composition of the present invention and where that tumor naturally lacks a surface CoCAM, as specifically exemplified for B7-1. The present invention also encompasses prophylactic methods for prevention of tumors or cancers, the method comprising the step of administering an immunogenic composition containing the tumor cell membrane (or tumor cell) preparation into which the GPI-anchored B7-1 fusion protein has been incorporated, in an amount effective for generating a cytotoxic immune response specific for the tumor or cancer cell. Optional additional ingredients in the immunotherapeutic composition include, without limitation, additional GPI-anchored costimulatory cell surface proteins and/or cytokines, e.g., IL-12 and optionally, IL-6.

BRIEF DESCRIPTION OF THE DRAWINGS

FIGS. 13A–13B illustrate the results of sodium dodecyl sulfate-polyacrylamide gel electrophoresis (SDS-PAGE) of purified GPI-B7.1. From a typical elution pattern, 10 $\mu$l of each fraction 1–7 (lanes 1–7) was subjected to SDS-PAGE. GPI-B7.1 purity was confirmed by silver stain (FIG. 13A) and western blot (FIG. 13B). Western blot was performed using the ECL Western Blotting Analysis system and 0.5 $\mu$g/ml of purified anti-human B7 mAb as the primary antibody.

FIG. 17A demonstrates that B7.1 transfected RCC-1 cells induce autologous antitumor CTL activity. Autologous T cells were co-cultured with irradiated RCC-1B7 cells at a 5:1 ratio for 7 days, then boosted with irradiated RCC-1B7 cells for an additional 5 days in the presence of 3 units/ml of IL-2. The live T cells were harvested by Histopaque-1077 discontinuous gradient centrifugation at 450 g for 20 min. Four hour CTL assays were carried out at different T cell/RCC-1 (E/T) ratios. FIG. 17B shows that anti-CD8 mAb and complement treatment abolished the CTL activity induced by RCC-1B7. The effector cells were preincubated or 1 h at 37° C. with anti-CD8 mAb and rabbit complement, washed, and mixed with target cells and the CTL assays were carried out.

FIGS. 17C–17D show that immunization with GPI-B7-1 incorporated membranes of EG7 cells induces a T cell proliferative response to the parental tumor. For FIG. 17C, EG7 tumor membranes were prepared as described in Example 8 and incubated with 10 $\mu$g/ml GPI-B7. Protein was detected by ELISA on membranes. Absorbance of M1/42 (anti-class I) binding wells was designated as 1.0. GPI-B7 incorporation was normalized to M1/42 binding. For FIG. 17D, C57BL/6 mice were immunized intraperitoneally (i.p.) with either HBSS or 100 $\mu$g of membrane equivalent protein of EG7 membranes alone or GPI-B7 incorporated EG7 membranes. Three weeks after the immunizations, T cells were purified from spleens and cocultured with irradiated (15,000 rads) EG7 cells for 5 days. All wells were pulsed with 1 $\mu$Ci of [$^3$H]-thymidine for the last 18 hours of culture. These results are representative of two independent experiments.

FIGS. 16A–16D show that immunization with GPI-B7-1 incorporated membranes induced CTL activity toward the parental tumor. In FIG. 16A, mice were immunized with either HBSS (squares), EG7 membranes (diamonds), or EG7 membranes incorporated with GPI-B7-1 (circles) as described in the Examples. After in vitro restimulation, the live cells were recovered and used as effector cells at various E:T ratios in a standard 4 hour $^{51}$Cr release assay with EG7 targets. In FIG. 16B, C57BL/6 mice were immunized with the addition of recombinant IL-12 (rIL-12). One week after the initial membrane injections, mice were given 2 ng rIL-12 i.p. every 4th day for two weeks. The T cells obtained from mice immunized with HBSS (squares), EG7 membranes (diamonds), EG7 membranes with GPI-B7 (CD16B) incorporated (circles), and EG7 membranes with GPI-B7 (LFA-3) incorporated (triangles) were restimulated in vitro with irradiated EG7 cells for five days. The live cells, after the 5 day culture, were used in a $^{51}$Cr release assay with EG7 cells (closed symbols) and autologous splenocytes (open symbols) that were treated with 10 ng/ml Concanavalin A (Sigma) for three days. In FIG. 16C, the immunization protocol was the same as described in FIG. 16B, except one group of mice was immunized with EG7 membranes that were incorporated with CD16B. CTL activity against EG7 cells, T cells recovered from mice immunized with HBSS (squares), EG7 membranes (diamonds), EG7 membranes with incorporated GPI-B7 (circles) or EG7 membranes with incorporated CD16B (triangles), was measured in a 4 hour $^{51}$Cr release assay. In FIG. 16D, mice were immunized with HBSS (squares), EG7 membranes (diamonds), EG7 membranes incorporated with GPI-B7 (closed circles) and T cells were restimulated in vitro as described. After the 5 day in vitro stimulation, live cells were recovered and used in a $^{51}$Cr release assay with EG7 targets. Some of the T cells obtained from mice immunized with EG7 membranes incorporated with GPI-B7 were treated with 53.6 (anti-CD8) mAb and rabbit complement for 45 minutes at 37° C. The live cells (open circles) were then recovered and used as effector cells in the same assay.

DETAILED DESCRIPTION OF THE INVENTION

Figures 1A, 1B:
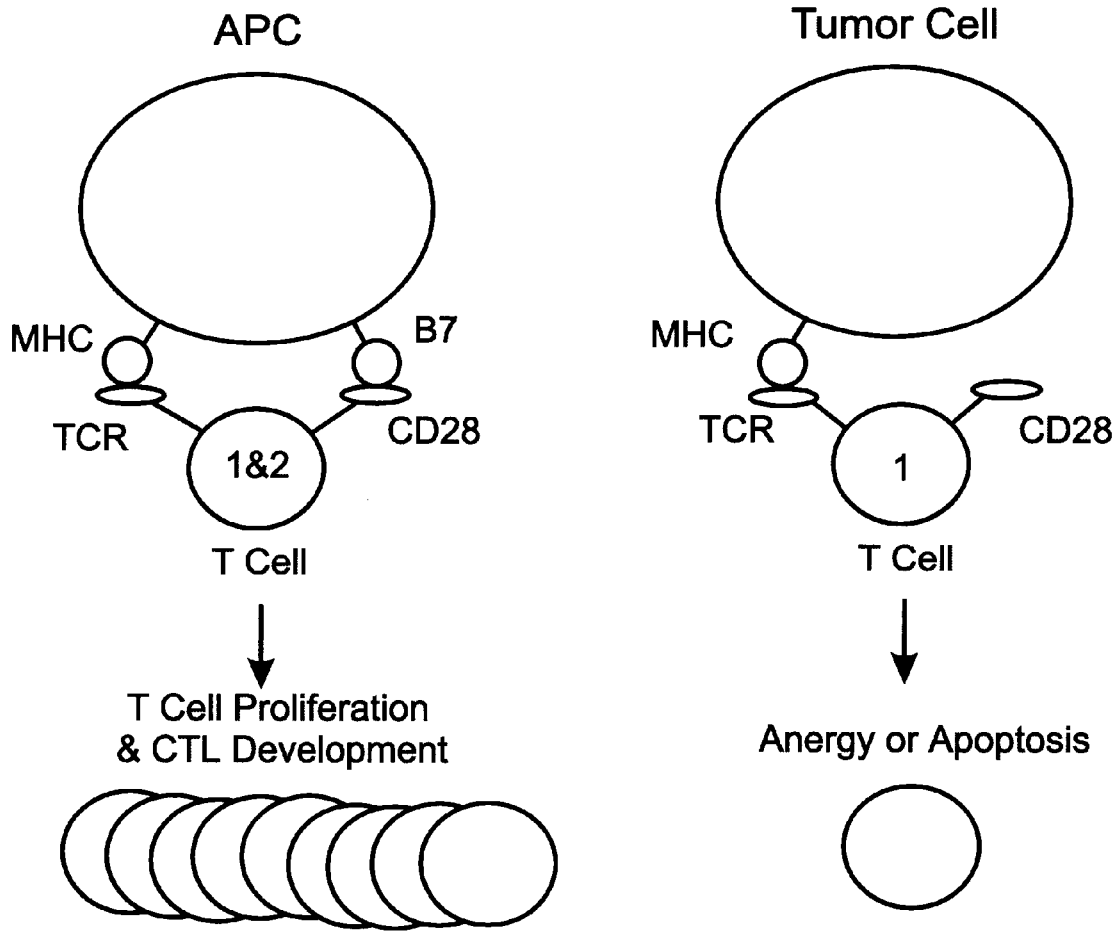
FIG. 1 schematically illustrates the two signals necessary for T cell proliferation.
Figure 2:
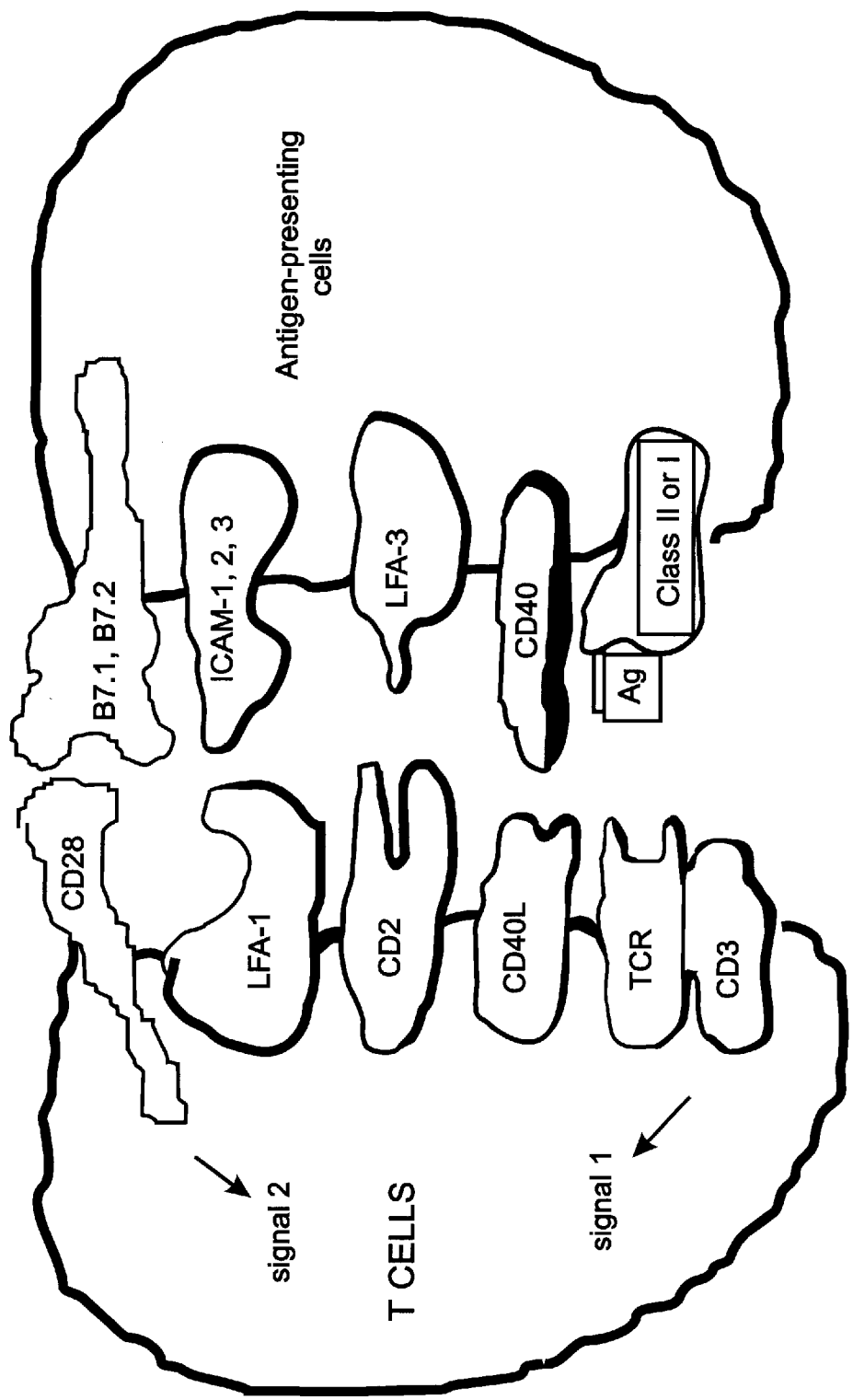
FIG. 2 schematically illustrates cell surface molecules involved in the interactions of T cells with other cells.

Tumor immunity is a major mechanism for elimination of tumors from the body. Such immunity is mediated by cytotoxic cells as activated natural killer (NK) cells and cytolytic T cells (CTL) that recognize tumors and destroy them. Virus-infected cells and parasite-infected cells are likewise destroyed by the cytotoxic cells. There are many ways by which tumor (or other detrimental) cells may circumvent immunosurveillance. One is the induction of anergy in tumor-specific T cells, which prevents tumor-specific CTL development, or by the lack or down regulation of molecules involved in T cell recognition and response to antigens. In order to generate optimal cytolytic immune response, antigen-specific T cells require at least two specific signals from antigen-presenting cells. One of the signals is provided by engagement of the TCR with peptide bearing MHC molecules on APC. Second signals (costimulatory signals) can be delivered by the interaction of various adhesion molecules on the surfaces of the T cells and the APCs, one of which is the interaction of CD28 expressed on the T cells and B7 expressed on APCs. The absence of a second signal results in T cell clonal anergy, thus preventing the development of tumor-specific CTL. It has been shown that tumor cells which lack B7 are poorly immunogenic because they fail to deliver the costimulatory signal for the generation of the appropriate immune response.

One approach to improve tumor cell immunogenicity has been to introduce costimulatory adhesion molecules such as B7 onto the tumor surface by the introduction of heterologous DNA. This B7 expression results in the induction of tumor immunity and subsequent tumor rejection in animals [Chen et al. (1992) Cell 71,1093–1102; Townsend et al. (1993) Science 259, 368–370; Li et al. (1994) J. Immunol. 153,421–428; Chen et al. (1994) J. Exp. Med. 179, 523–532]. Ostrand-Rosenberg and coworkers have demonstrated that regression of established tumors can be achieved by vaccinating a mouse animal model with tumor cells expressing B7-1 and both the MHC molecules [Baskar et al. (1995) J. Exp. Med. 181, 619–629].

The costimulatory signal is required only during the initiation phase but not for the effector phase of the antitumor T cell responses. Thus, the CTLs induced by the B7 transfected tumor cells can kill and reject the parental tumor cells without a requirement for B7 expression by the tumor cells. The present inventors have confirmed these observations in a human autologous system using a B7-1-transfected renal carcinoma cell line and in a mouse system using transfected melanoma cells [Wang et al. (1995), supra].

Potential disadvantages of the genetic manipulation approach to the display of the B7 phenotype on the tumor cell surface include the difficulty of genetic manipulation of a variety of cell types, especially when the cells are prepared from freshly isolated tumor tissue, the time-consuming nature of such manipulations, and the difficulty in regulating the amount of the recombinantly-expressed B7 on the tumor cell surface. In addition, most techniques currently available for the genetic modification of animal (including human) cells are based on vectors of viral origin and there are associated health and safety concerns, especially in the course of cancer therapy in human patients. Additionally, where viral vectors (and other vectors as well) are used to introduce GPI/B7 coding sequences, there is the potential for an immune response to vector-encoded protein(s). Thus, the present inventors have developed compositions and methods based on the introduction of purified GPI-B7 into tumor cells or tumor cell membranes in vitro and use of such GPI-B7-modified cells or membranes in immunotherapeutic compositions and methods as well as in immunogenic compositions and methods for prevention of tumors.

Many proteins are anchored to the membrane via a transmembrane domain. Some proteins are linked by a moiety called glycosyl-phosphatidyl inositol (GPI) [Low and Saltiel (1988) Science 239, 268–275]. Within the GPI moiety is a lipid tail which anchors the protein to the outer leaflet of the lipid bilayer. A bacterial enzyme called phosphatidyl inositol specific phospholipase C (PIPLC) is able to remove GPI-anchored proteins from the cell membrane. Humans do not have an equivalent enzyme, except PIPLD, which is inactive in the physiologic state [Low and Prasad (1988) Proc. Natl. Acad. Sci. USA 85, 980–984].

Figure 3:
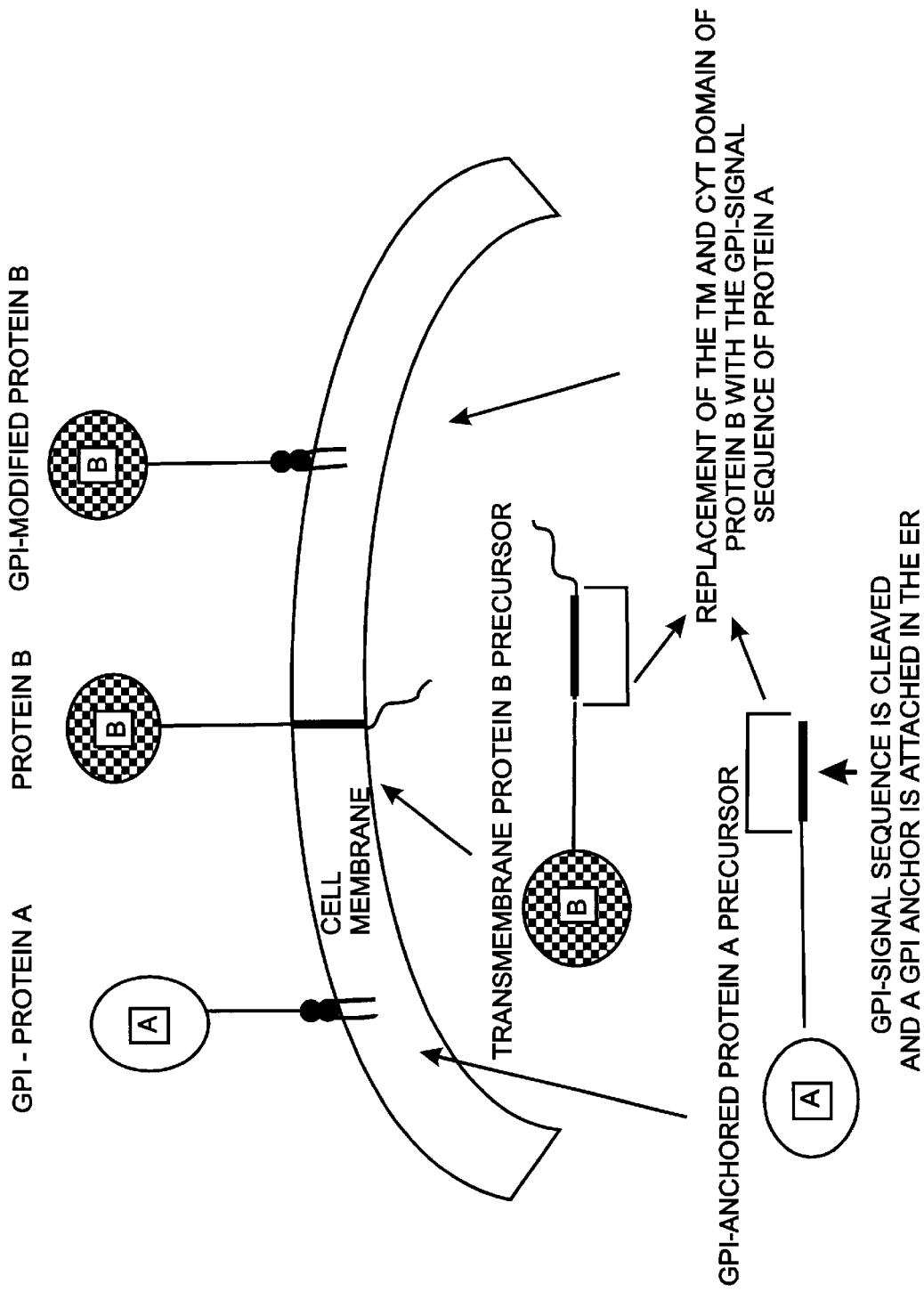
FIG. 3 illustrates the modification of transmembrane proteins to have GPI anchors.

Most surface molecules are not GPI-anchored but are polypeptide-anchored transmembrane proteins. Many studies have shown that it is possible to interconvert these membrane isoforms by molecular biological techniques. Through the consensus signal sequence for GPI-anchor attachment has not been identified, the site attachment of GPI-anchor to the protein has been studied in detail [Low, M. G. (1989) Biochem. Biophys. Acta 988, 427–454; Waneck et al. (1988) Science 241, 697–699; Caras et al. (1987) Science 238, 1280–1283; Tykocinski et al. (1988) Proc. Natl. Acad. Sci. USA 85, 3555–3559; Waneck et al. (1988) Proc. Natl. Acad. Sci. USA 85, 577–581]. When synthesized in the endoplasmic reticulum, GPI-anchored proteins each contain a short hydrophobic domain with no hydrophilic cytoplasmic domain in the C-terminal end. Once synthesis is complete, the hydrophobic domain is removed by enzymatic cleavage and replaced, via a transamidation reaction, with a preformed GPI moiety and subsequently transported to the cell surface. The signal sequence for GPI-anchor attachment is found at the hydrophobic C-terminal end of precursors of the GPI-anchor. Thus, by replacing the transmembrane and cytoplasmic domains with the carboxy terminal end of the precursor GPI-anchored protein, a transmembrane surface protein can be converted to a GPI-anchored protein (FIG. 3). This signal sequence usually includes the amino acids spanning from the GPI-anchor attachment site to the C-terminal hydrophobic end found in the precursor of GPI-anchored proteins.

Figure 4:
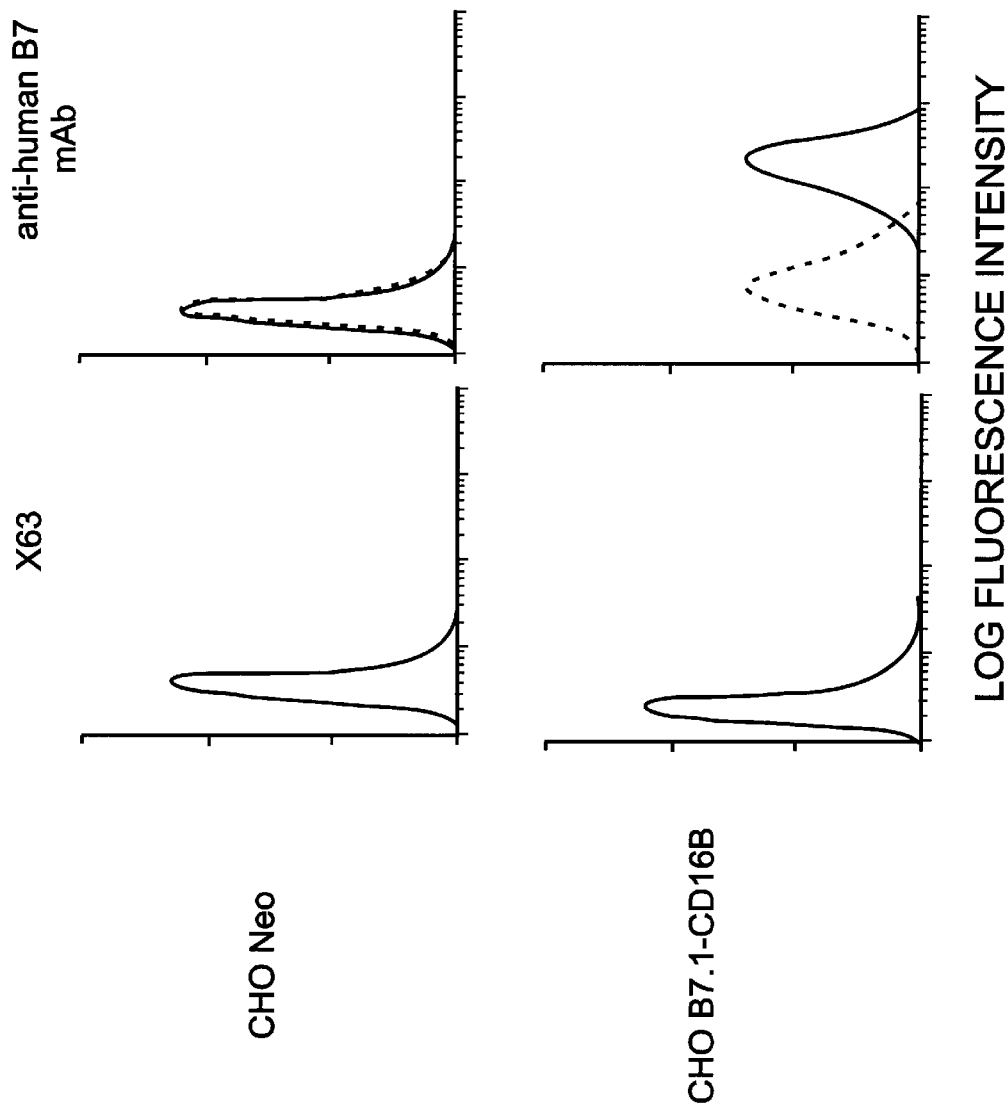
FIG. 4 demonstrates the expression of GPI-anchored B7 in Chinese Hamster Ovary (CHO) cell transfectants (CHO B7.1-CD16B) as compared to control cells not expressing a B7-1/CD16 fusion protein (CHO Neo). Flow cytometry analysis was carried using anti-human B7 MAb (MAb, monoclonal antibody) and FITC-labeled goat anti-mouse Ab. X63 is a non binding IgG control. The dotted lines represent expression of B7 after phosphatidylinositol-specific phospholipase C (PIPLC) treatment.
Figure 5A:
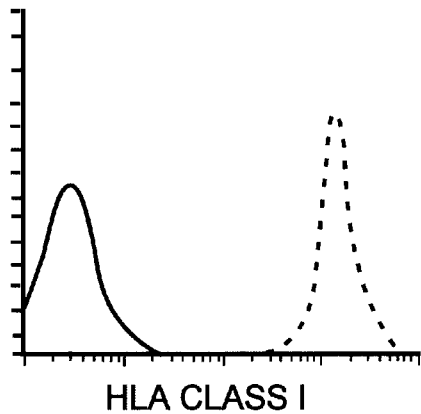
FIGS. 5A–5D illustrate the expression of B7-1 on freshly isolated breast cancer cells by protein transfer using purified GPI-B7.1. Human breast tumor tissue was obtained by surgical resection, followed by collagenase treatment. Water lysis was used to remove blood cells from the tumor cell suspension. The remaining tumor cells were resuspended to a concentration of $5\times10^6$ cells/ml in RPMI 1640 containing 5 mM EDTA and 1 mg/ml of ovalbumin. They were incubated for 1.5 h at 37° C. with 20 mg/ml GPI-B7.1. The cells were then washed with PBS and prepared for flow cytometric analysis. The cells were stained with either the negative control antibody, X63 (solid line); W6/32 (anti-human class I); IVA12 (anti-human class II) or PSRM-3 (anti-human B7-1) antibody.
Figure 5B:
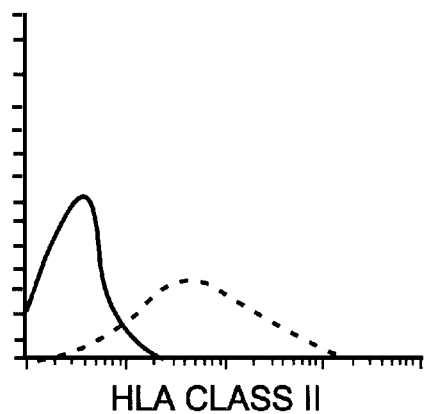
Figure 5C:
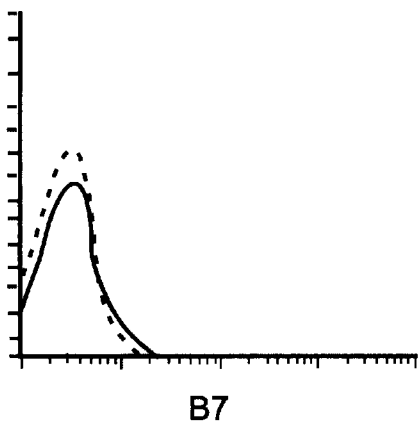
Figure 5D:
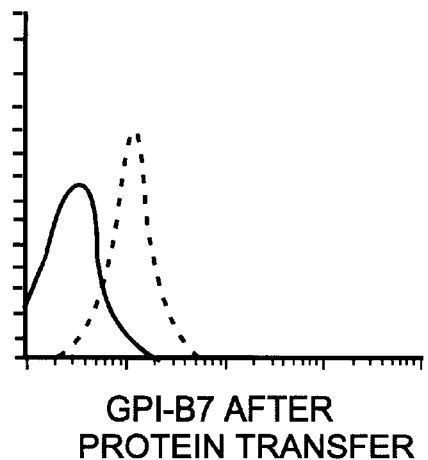
Figure 11:
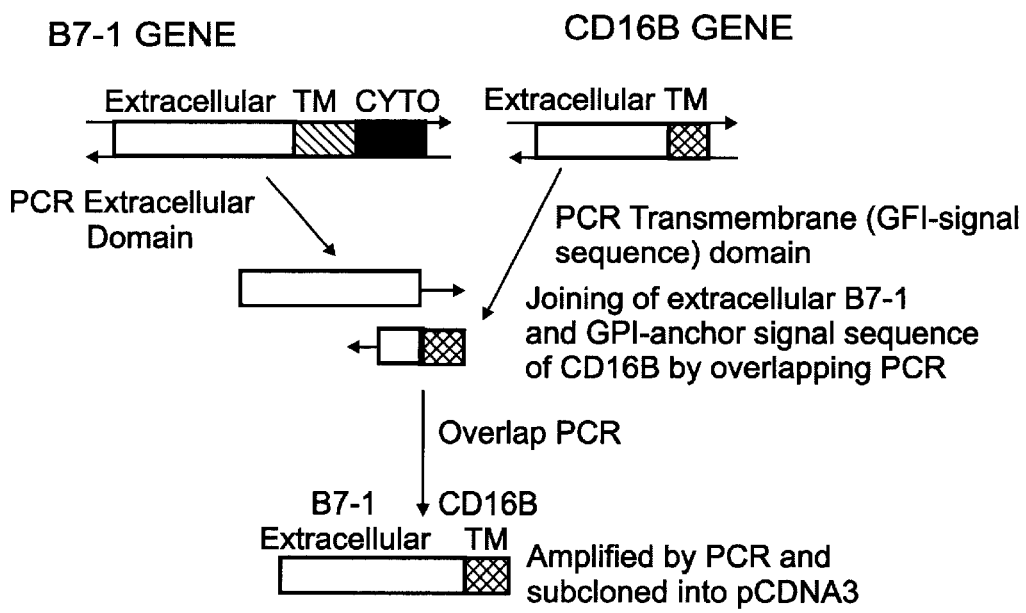
FIG. 11 is a schematic representation of polymerase chain reaction (PCR) products resulting from the construction of the chimeric B7-1-CD16B molecule described in the Examples. TM, transmembrane domain, CYTO, cytoplasmic domain.

The chimeric B7.1-CD16B molecule specifically exemplified herein was created by overlap PCR as described in hereinbelow and represented in FIG. 11. PIPLC, which is known to cleave GPI-anchored proteins expressed on the cell surface [Low and Saltiel (1988) Science 239, 268–275], was used to confirm that the newly constructed B7-1-CD16B chimera was anchored on the cell surface by a GPI anchor. As seen by flow cytometry (FIG. 4), nearly 99% of the B7.1-CD16B molecules expressed on CHO cells were released by PIPLC treatment. Under similar conditions, polypeptide-anchored B7.1, as expressed on the human B-cell line JY, was unaffected. The B7.1-CD16B molecule is also referred to as GPI-B7 herein.

Figure 12:
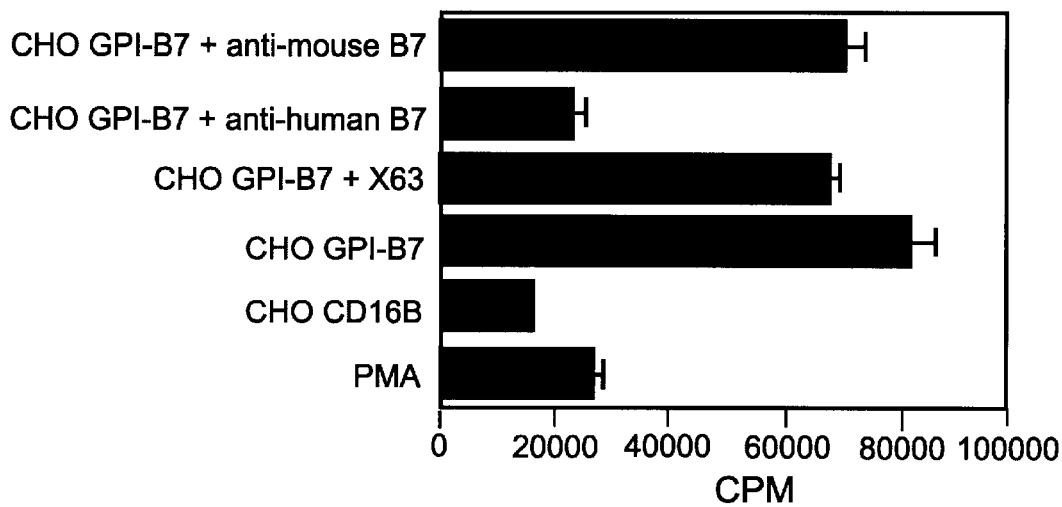
FIG. 12 shows that GPI-B7.1 expressed on CHO cells provides T cell costimulation. CHO CD16B and CHO GPI-B7.1 were irradiated (8,000 rads) and incubated with either control mAbs, X63 and anti-mouse B7, or the blocking mAb, anti-human B7. These cells were incubated for three days with $10^5$ T cells at a ratio of 8:1 T cells:CHO cells. The cultures were pulsed with 1 $\mu$Ci [$^3$H]-thymidine for the last 6 h of the incubation.
Figure 13:
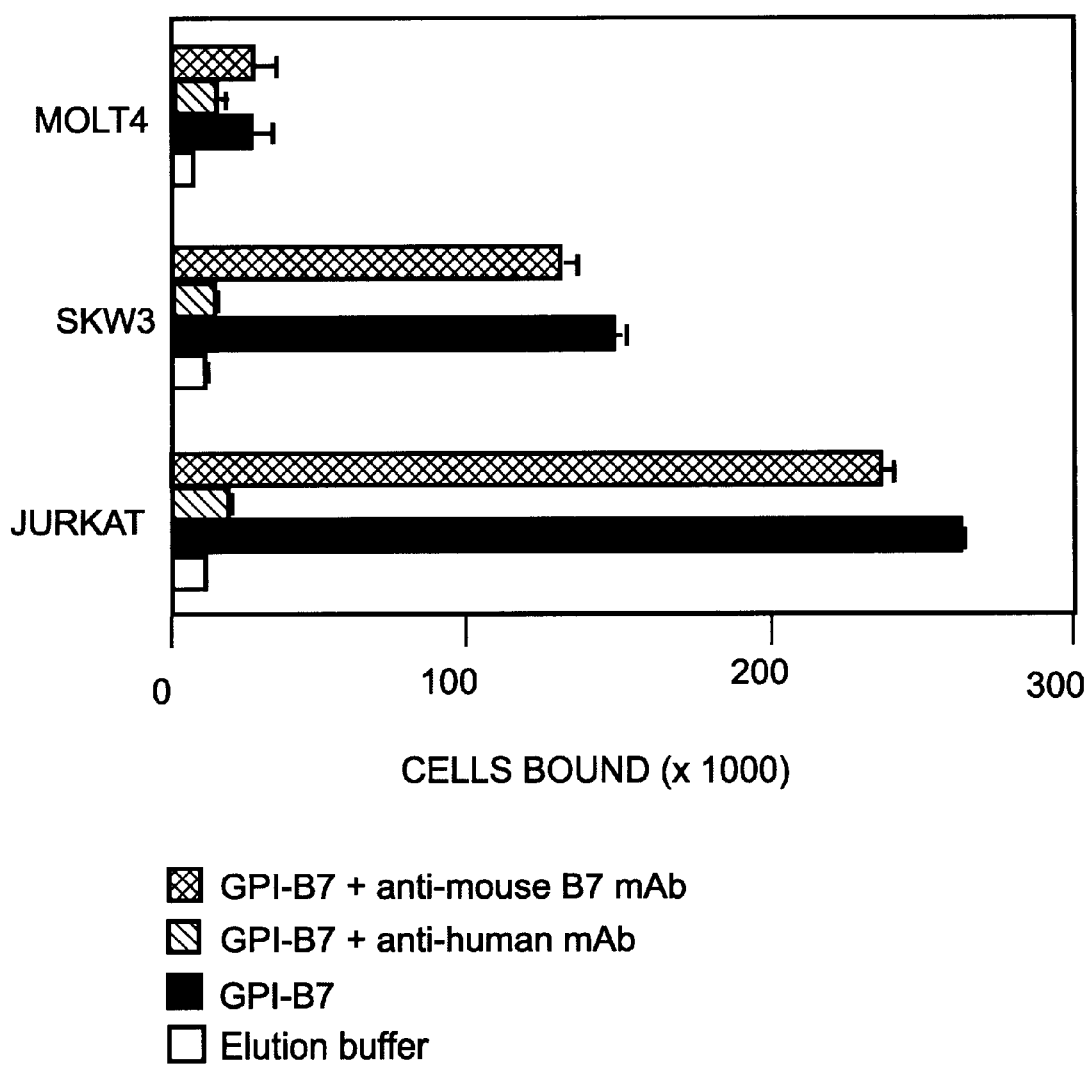
FIG. 13 graphically illustrates that purified GPI-B7.1 binds CD28 expressing cells. $^{51}$Cr labeled Jurkat, SKW3, and MOLT4 cells were allowed to bind GPI-B7.1 coated microtiter wells, in the presence or absence of anti-human or anti-mouse B7 mAbs, for 1 h at 4° C. The nonadherent cells were removed by plate inversion, and the adherent cells were counted and the data were converted to cells bound/well.
Figure 14A:
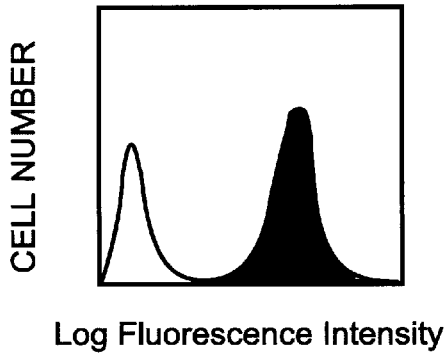
FIGS. 14A–14F demonstrate that GPI-B7.1 reconstitutes various tumor cell lines. Tumor cells were washed and resuspended to $10^7$ cells/ml in PBS/EDTA. They were then incubated for 2 h at 37° C. with 10 $\mu$g/ml of purified GPI-B7.1. Reconstituted tumor cells included Jurkat, K1735, Ramos, T47D, WM115 and SKMEL28 (FIGS. 14A, 14B, 14C, 14D, 14E and 14F, respectively). Histograms represent B7.1 expression before (white) and after (dark) membrane reconstitution with GPI-B7.1. The negative binding control antibody, X63, is represented by the dotted line. B7-1 on the cell surface was measured by fluorescence activated cell sorting (FACS).
Figure 14B:
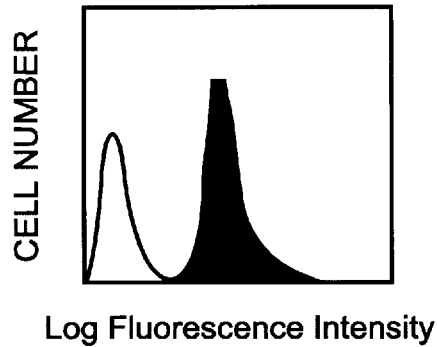
Figure 14C:
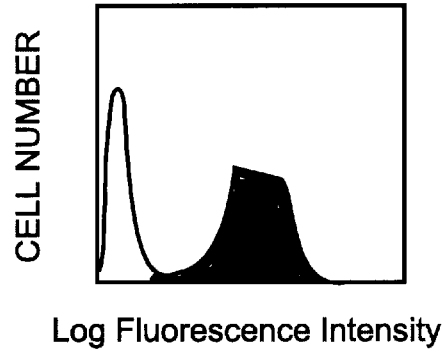
Figure 14D:
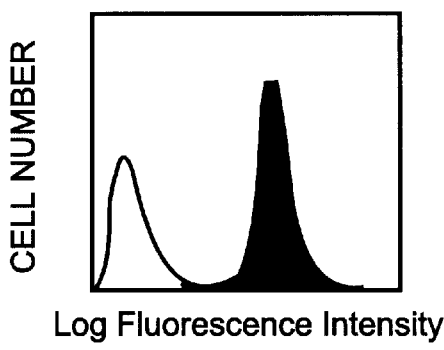
Figure 14E:
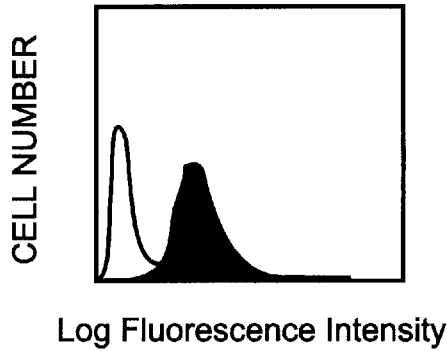
Figure 14F:
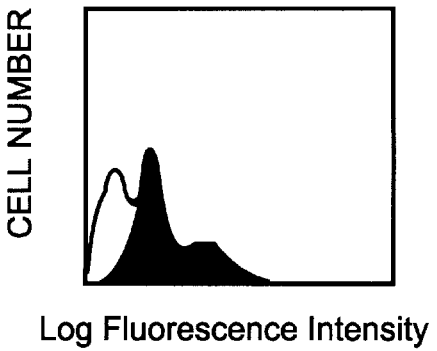

Polypeptide-anchored B7-1 has been shown to provide potent polyclonal stimulation of T cells when present on CHO cells [Linsley et al. (1991) J. Exp. Med. 173, 721–730] and P815 [Azuma et al. (1992) J. Exp. Med. 175, 353–360]. As shown in FIG. 12, CHO GPI-B7 cells are able to provide costimulation in cooperation with PMA to induce polyclonal activation. This stimulation can be blocked by the addition of anti-human B7-1 mAb; however, the control mAbs X63 and anti-mouse B7-1 are unable to block the polyclonal proliferation of the T cells. Under similar conditions, CHO CD16B cells are unable to induce T-cell proliferation. To compare the effect of the two different anchor mechanisms for B7-1, RCC-1 B7 and RCC-1 GPI-B7 were used to stimulate T cells in an allogeneic system. GPI-B7 was shown to be as efficient as transmembrane B7 in providing T-cell costimulation.

GPI-B7 was purified by affinity chromatography from a CHO CPI-B7 cell detergent lysate. Silver staining and Western blot after sodium dodecyl sulfate-polyacrylamide get electrophoresis after elution from the anti-human B7-1 mAb-coupled Sepharose column indicate the molecular mass of GPI-B7 to be approximately 55–71 kDa.

Human B7-1 has been shown to bind both cell-associated CD28 [Linsley et al. (1990) *Proc. Natl. Acad. Sci. USA* 87, 5031–5035] and soluble CTLA41g [Linsley et al. (1991) supra]. To verify that GPI-B7 is functional after purification, we tested the ability of the cell lines Jurkat, SKW3, and MOLT4, which have different degrees of CD28 expression, to bind purified GPI-B7-coated microtiter wells. As shown in FIGS. 14A–14F, Jurkat and SKW3, both having significant CD28 expression, could bind to the GPI-B7-coated wells, with very little background binding. This binding could be specifically blocked by the addition of anti-human B7-1 mAb, whereas the anti-mouse B7-1 mAb is unable to block cell binding. MOLT4, which expresses very low amounts of CD28, minimally bound to GPI-B7-coated wells.

We determined that GPI-B7 can be incorporated into cell membranes of tumor cell lines. The mouse melanoma cell line K1735, human β- and T-lymphoma cell lines Ramos and Jurkat, and the human breast carcinoma cell line T47D were incubated with purified GPI-B7 at 10 µg/ml in PBS/EDTA. The human melanoma cell liens WM115 and SKMEL28 were mixed with a different purified preparation of GPI-B7 at 6 µg/ml and 40 µg/ml, respectively. GPI-B7 was able to reconstitute expression of all cell lines tested to various degrees (FIGS. 14A–14F). FIG. 5 shows that GPI-B7-1 can also incorporate within the membrane of primary breast tumor tissue freshly obtained from surgical resection). This incorporation is due to the GPI anchor, as addition of PIPLC to the reconstituted cell results in significant reduction of GPI-B47 expression. Time and temperature are also factors, with optimum conditions being 37° C. for 2 h. In addition, increasing the concentration of GPI-B7 increases the amount of incorporated material. However, the ability of individual purified preparations of GPI-B7 to incorporate itself into membranes varies; therefore the concentrations are optimized on chicken red blood cells prior to tumor cell reconstitution.

Cell lines such as SKMEL28 (FIG. 14F) vary in their ability to incorporate the GPI-anchored material. This cell line is extremely adherent and tends to clump and settle down during the procedure. This could limit uniform access of the purified GPI-B7 to all cells, therefore resulting in bimodal incorporation with a population of cells having an increased expression of GPI-B7.

Figure 6:
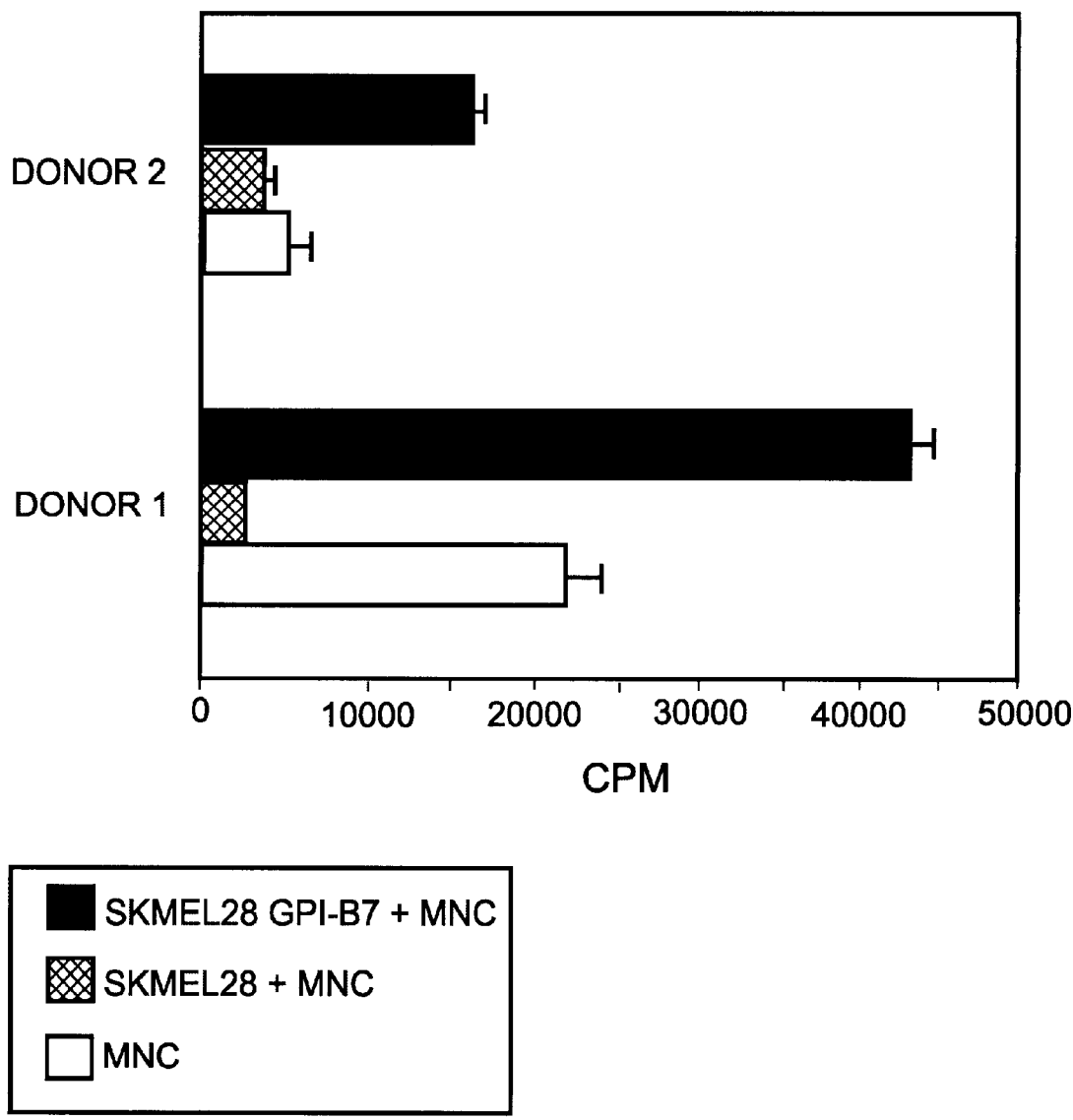
FIG. 6 demonstrates that GPI-B7 modified melanoma cells stimulate T cells in an allogeneic mixed lymphocyte tumor response (MLTR). Unmodified and GPI-B7 modified tumors were irradiated and added to allogeneic mononuclear cells (MNC). T cell proliferation was measured using the [$^3$H]-thymidine incorporation method. Tumor cells were washed and resuspended in PBS/EDTA at $10^7$ cells/ml. These cells were incubated for 2 h at 37° C. with 40 μg/ml of GPI-B7.1. After reconstitution, the tumors were washed and irradiated (10,000 rads). In a MLTR, $5\times10^4$ tumor cells were incubated with $2\times10^5$ peripheral blood mononuclear cells (PBMC). After three days, the cultures were boosted with $5\times10^4$ tumor cells, either reconstituted or untreated, and incubated for an additional four days. All cultures with pulsed with [$^3$H]-thymidine for the last 18 h of the assay.
Figure 7:
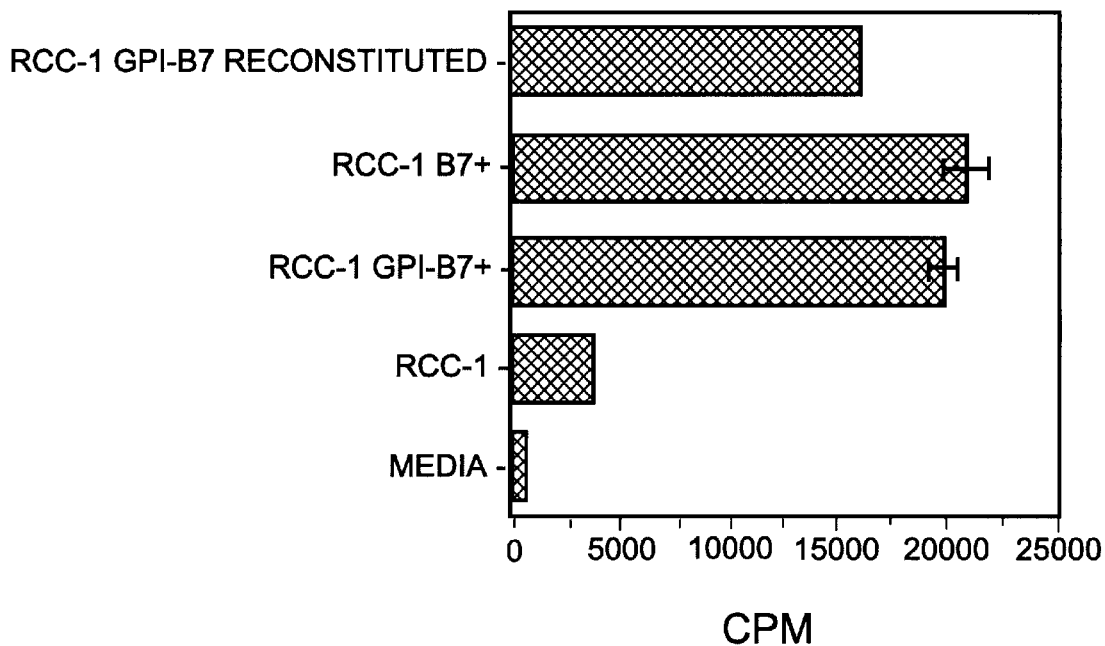
FIG. 7 shows that reconstituted GPI-B7 is as efficient as transfected B7 or GPI-B7 in stimulating allogenic T cells. Irradiated RCC-1, RCC-1 B7+, RCC-1 GPI-B7+ or RCC-1 incorporated with 20 μg/ml GPI-B7 were cocultured with purified allogenic T cells for 3 days. At day three, the cultures were boosted with the same tumor cells and incubated for an additional two days. T cell proliferation was measured by [$^3$H]-thymidine pulsing the last 18 hours of the incubation.

FIG. 6 shows that little proliferation of MNCs from two donors results from coculture of SKMEL28 cells or control MNC culture. MNCs cocultured with GPI-B7-1 reconstituted SKMEL28 cells gave a strong proliferative response in both donors. Differences in the magnitude of proliferation between donors is believed due to differences in allogenic responses. GPI-B7-1-modified tumors were also compared to tumor cells (using the renal carcinoma cell line RCC-1) transfected with GPI-B7-1 as well as transmembrane B7-1. The RCC-1 cell line expresses MHC class I, ICAM-1 and LFA3 but not B7-1. FIG. 7 shows that all three were able to stimulate T cell proliferation. This confirms that the purified reconstituted molecule is as efficient as the transfected molecule and that T cells can be stimulated in vitro by the "protein transfer" method (the spontaneous incorporation of a GPI anchor-containing protein from the medium into cell membranes; this occurs either in the intact cell membrane, in an irradiated cell membrane or in isolated cell membranes.

Figure 8A:
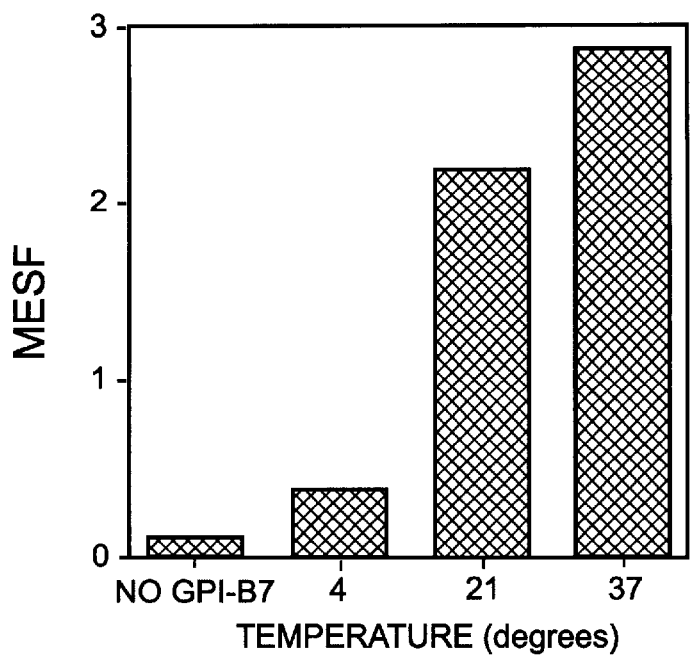
FIG. 8A shows the effect of temperature on incorporation of GPI-B7. Ramos cells at a concentration of $10^7$ cells/ml were incubated with either no GPI-B7 or GPI-B7 at a final concentration of 10 μg/ml. GPI-B7 was incubated with Ramos cells at various temperatures for 2 hours. The control containing no GPI-B7 was incubated for 2 hours at 37° C. Incorporation was detected by flow cytometry.
Figure 8B:
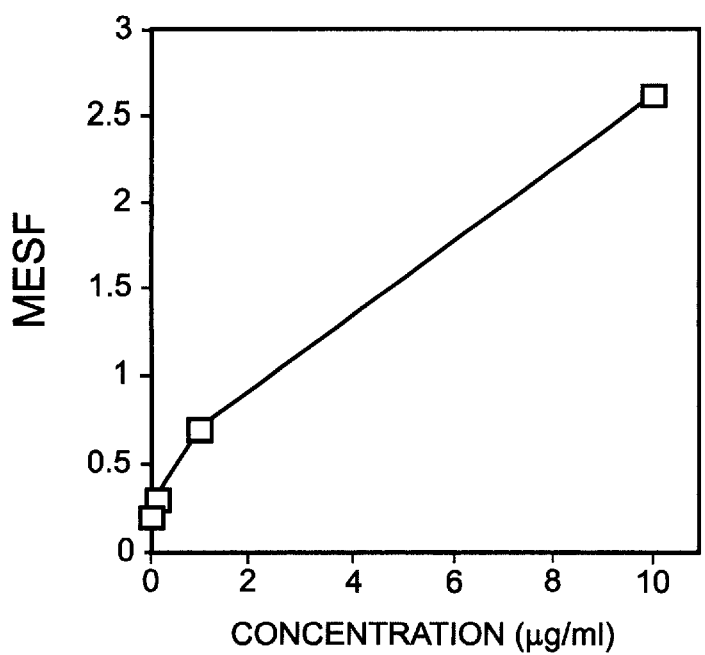
FIG. 8B shows the effect of concentration on incorporation of GPI-B7. Ramos cells were prepared as described above and incubated with various concentrations of GPI-B7 for 2 hours at 37° C. Incorporation was detected by flow cytometry.
Figure 9:
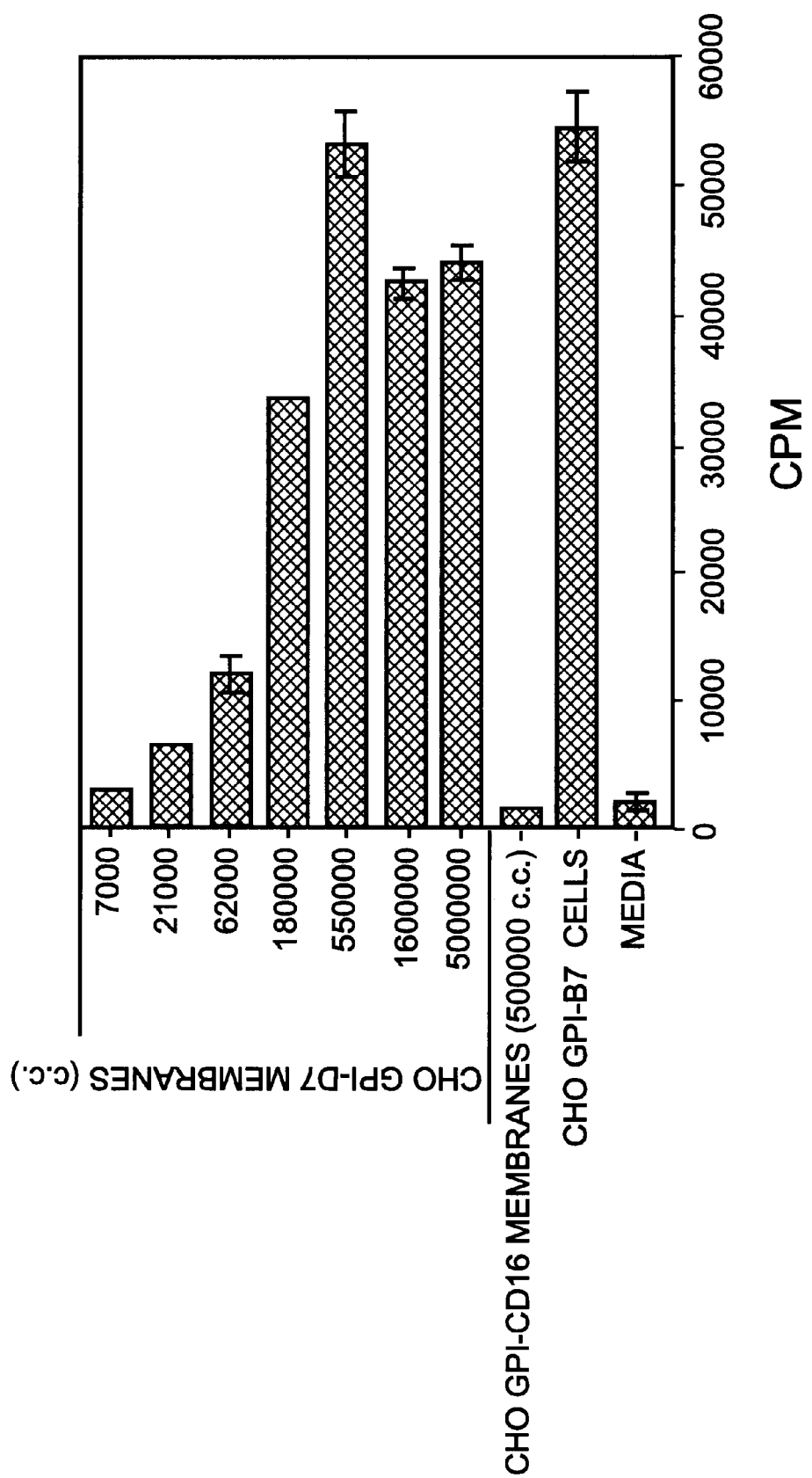
FIG. 9 illustrates that GPI-B7 present on cell membrane preparations can stimulate T cells. Membranes of CHO cells expressing GPI-B7 or CD16B were prepared and various cell equivalent (c.e.) concentrations were cocultured with purified T cells in the presence of 1 μg/ml PMA for 3 days. T cell proliferation was measured by [$^3$H]-thymidine pulsing during the last 6 hours of the incubation. As a comparison and positive control, $1.25\times10^4$ CHO cells transfected with GPI-B7 were also cocultured with purified T cells.
Figure 10:
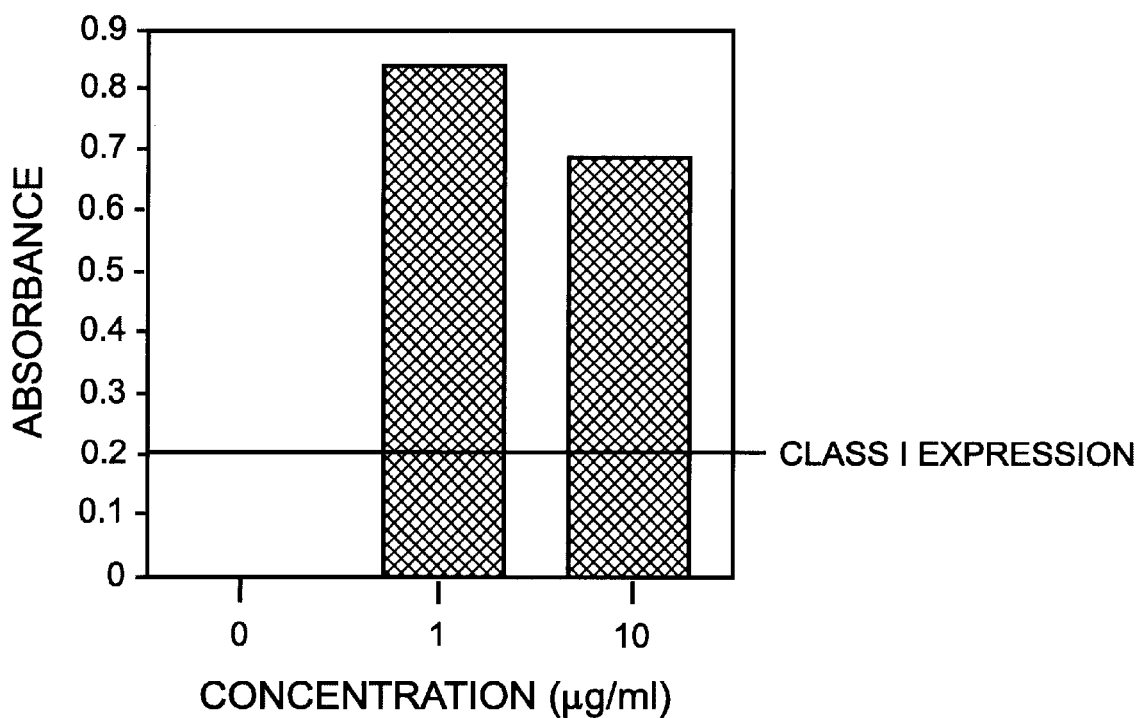
FIG. 10 shows the incorporation of GPI-B7 into tumor cell membrane preparations. K1735M2 cell membranes were prepared and incubated with various concentrations of purified GPI-B7 for 2 hours at 37° C. The reconstituted membranes were then washed and coated onto ELISA plates overnight. Incorporated GPI-B7 as well as natively expressed MHC class I was detected by ELISA.

As seen in FIG. 8A, incorporation of a GPI-B7-1 fusion protein within cell membranes is efficient at 37° C. and at room temperature, but it is severely curtailed at 4° C. In the Ramos cells, the cell-associated fusion protein was significantly sensitive to release by PIPLC. In Jurkat cells (a T lymphoma expressing CD28 and CTLA4 surface antigens) there was only partial release of the anchored fusion protein by PIPLC, indicating that part of the fusion protein associated with the surface of these cells is due to binding of the purified fusion protein to the CD28 or CTLA4 antigens on the surface of those cells rather than the result of the anchor insertion into the cell membrane. Without wishing to be bound by theory, it is believed that incorporation within the membrane of the GPI anchor is dependent on membrane fluidity. It is noted that serum proteins appear to interfere with the incorporation into cell membranes of GPI anchor-containing proteins. It is further noted that incubation for incorporation of these GPI-anchor containing proteins preferably does not extend past the lifetime of the cells in a serum-free environment.

Expression of GPI-B7 on actively proliferating cells was transient, with 72% of GPI-B7 lost after 24 h during normal in vitro culture conditions, but there is still expression over immunotherapeutic compositions of the present invention and their use in the methods of the present invention can create the optimal target to facilitate many T-cell regulatory and effector functions needed for tumor immunity. Through the use of a GPI anchor, these molecules can be quickly tested, individually and in cooperation with others, to determine the most effective combination needed to create an immunogenic tumor cell or membrane preparation for use in individual therapy or prophylaxis of animal and/or human tumors.

Confirming that purified GPI-B7 can bind CD28$^+$ cells and incorporate itself into tumor cell membranes, we then determined that GPI-B7 works in concert with the surface MHC molecules on tumor cells to provide a costimulatory signal. The human melanoma cell line SKMEL28 was chosen because it lacked B7 but had significant expression of both class I and class II MHC molecules. Untreated SKMEL28 cells were unable to elicit an immune response, as measured by thymidine incorporation (FIG. 6). Upon reconstitution of B7 expression with GPI-B7 at 40 µg/ml, the SKMEL28 cells induced a significant increase in T-cell proliferation in both donors. These results indicate that GPI-B7 can functionally reconstitute B7.1 expression onto the surface of tumor cells and provide the secondary signal needed for the production of tumor immunity.

The GPI anchor domain of LFA3 appears to have potential advantages over the GPI anchor domain of CD16B. That from LFA3 reconstitutes significantly better into tumor cells and cell membranes when compared with the corresponding CD16B-derived GPI anchor domain. Without wishing to be bound by theory, it is believed that the LFA3 GPI anchor provides more stable incorporation within the cell membrane in that there is evidence that the region of the fusion between B7.1 and the LFA3 GPI anchor domain is less susceptible to proteolytic cleavage (and release from the membrane) than the GPI anchor domain of CD16B.

ICAM-1, the ligand of LFA-1, has been shown to be a costimulatory molecule for T cell proliferation [Springer, T. A. (1990) Nature 346, 425–434; van Seventer et al. (1990) J. Immunol. 144, 4579–4586; Damle et al. (1992) J. Immunol. 148, 1985–1992]. Like the B7.1 molecule, the expression of ICAM-1 on tumors such as melanomas results in tumor rejection. The effect of a GPI-anchored ICAM-1 is determined using parallel techniques to those presented herein for its incorporation into tumor cell membranes and ability to ameliorate an immunogenic response to tumor cells. Such a fusion protein has been described by Staunton et al. (1992) J. Immunol. 148, 3271–3274. After expression in recombinant CHO cells, the ICAM-1 fusion protein is purified as described [McHugh et al. (1995) Proc. Natl. Acad. Sci. USA 92, 8059–8063] except that during column elution, octyl glucoside is used, a detergent which can be removed using Centricon concentrators. The ICAM-1 coding and amino acid sequences are presented in FIGS. 11A–11C of U.S. Pat. No. 5,506,126 [Seed and Aruffo, filed Oct. 18, 1993].

Our results show that live tumor cells can be reconstituted with GPI-anchored molecules. Using GPI-B7.1 as a model system, we found that the level of reconstitution is directly proportional to the concentration of protein, time of incubation and temperature [Nagarajan et al. (1991) FASEB J. 5,A1718; Nagarajan et al. (1995) J. Immunol. Meth. 184, 241–251]. The potential advantage of reconstituting actively proliferating cells is that cellular functions of reconstituted molecules can be studied in live cells. However, for human immunotherapeutic purposes, live proliferating tumor cells are not advised since it is not prudent to inject live tumor cells into a patient. In addition, unlike gene transfected cell lines, the reconstituted cells cannot make new receptors to replace losses due to endocytosis or cell division. This results in a gradual decrease in the expression of reconstituted molecules.

Reduction in the density of GPI-anchored costimulatory proteins from the cell surface due to cell division is avoided by irradiating the cells. Preliminary experiments have shown that irradiation of tumor cells does not interfere with the incorporation of GPI-B7.1. However, one potential disadvantage is that immunogenicity of some of the B7.1 positive mouse tumors are affected by irradiation. Townsend et.al. (1994) Cancer Res. 54:6477–6483 showed that irradiation diminishes the effectiveness of B7.1 positive mouse melanoma tumor cells as immunogens. On the other hand, Baskar et al. (1994) Cell Immunol. 155(1):123–133 has shown that the irradiation does not affect the immunogenicity of B7.1 positive sarcomas. Our studies with HSA [Wang et al. (1995) Eur. J. Immunol. 25, 1163–1167] showed that irradiated melanoma cells can induce T cell responses in vitro. In humans, in vitro T cell responses against tumor cells were measured using irradiated tumor cells suggesting that they were not affected by irradiation.

Conditions for optimal incorporation of GPI-anchored molecules on irradiated cells are determined as follows. Tumor are irradiated by gamma irradiation, and parameters such as time, temperature, and concentration of proteins for optimum incorporation of GPI-anchored proteins are determined as described [Nagarajan et al. (1995) J. Immunol. Meth. 184(2), 241–251]. ELISA or FACS analysis is used to determine expression. A preliminary comparison of the stability of GPI-B7.1 reconstituted on live and irradiated cell membranes show that GPI-B7.1 reconstituted on irradiated cells remains for a longer duration under culture conditions; irradiated cell do not undergo cell division.

An alternative to irradiated tumor cells is a tumor cell membrane preparation. Isolated cell membranes do not proliferate or mediate endocytosis of surface proteins making them suitable targets for modification by GPI-anchored molecules. Tumor membranes appropriately prepared are also ideal for human immunization. Since both irradiated cells and isolated cell membranes can be modified with GPI-anchored molecules, preparations of immunogenic irradiated tumor cells or tumor cell membranes are made by modifying them with GPI-B7.1 or other costimulatory GPI-molecules.

Next, conditions for reconstitution of isolated tumor cell membranes are optimized. Cell membranes prepared from Th1 and Th2 cells have been shown to stimulate B cell proliferation and differentiation [Hodgkin et al. (1991) J. Immunol. 147:3696–3702; Hodgkin et al. (1991) J. Immunol. 145:2025; Noelle et al. (1991) J. Immunol. 146:1118] suggesting that cell membranes, like intact cells, can stimulate immune cells. Membranes are prepared essentially as described [Hodgkin et al. (1991) J. Immunol. 147:3696–3702; Maeda et al. (1983) Biochem. Biophys. Acta, 731:115–120]. All membrane preparations and reconstitutions are done using sterile solutions. Briefly, cells are homogenized in an ice cold buffer containing 20 mM Tris pH 8.0, 10 mM NaCl, 0.1 mM $MgCl_2$ and 0.1 mM PMSF using Polytron homogenizer. The homogenate is diluted 20 fold in the same buffer and overlaid on a 41% (v/w) sucrose cushion and centrifuged at 95,000 g for 1 h at 4° C. The fluffy interface is recovered, washed by centrifugation once at 95,000 for 20 min. at 4° C. and twice at 13,500 rpm for 30 min. at 4° C. The membranes are resuspended using a 20 gauge needle in RPMI containing 10 mM HEPES and antibiotics (penicillin and streptomycin). Membranes can be used immediately or can be frozen in liquid $N_2$ until further use. Freezing and thawing does not affect the immunostimulatory property of cell membranes [Hodgkin et al. (1991) J. Immunol. 147:3696–3702]. The quantity of membrane can be expressed in terms of cell equivalents or as total protein. The same parameters as described for live cells and irradiated cells are used to optimize conditions for incorporation of GPI molecules on isolated tumor membranes. Alternatively, cell membrane can also be prepared from tumor cells already modified to express GPI-B7.1 on the cell surface by GPI-protein transfer. As positive controls, membranes from GPI-B7.1 transfected cells are used. ELISA assays are used to determine the incorporation of GPI-B7.1 onto membranes. The membranes are lysed in Triton X-100 and coated on an ELISA plate. The GPI-B7.1 bound to the plate are quantitated using a primary antibody specific to that particular protein and a peroxidase conjugated secondary antibody. The ELISA readings are compared against the readings obtained from a membrane preparation obtained from GPI-B7.1 transfected CHO cells. Membranes and cells prepared from freshly obtained human tumors are also tested for reconstitution with GPI-B7.1 and the conditions optimized.

Since some tumors lose immunogenicity upon irradiation, tumor cell membranes isolated as described here serve as an alternate immunogen. Cell membranes are convenient because they are prepared from frozen tumor cells, reconstituted, and stored in aliquots for future use.

As shown in our preliminary studies, cell surface incorporated GPI-B7.1 retained its functional ability to induce T-cell proliferation. Incorporated GPI-B7.1 can induce CTL development in the in vitro human system and tumor immunity in vivo in mouse models. We have established K1735M2 (melanoma, C3H/HeN origin), P815 (mastocytoma, DBA/2 origin) and EL4 (Thymoma, C57BL/6) origin, transfectants expressing human GPI-B7.1 molecule. We have also obtained K1735P and its MHC Class I and Class II transfectants from H. Ananthaswamy, M.D., Anderson Cancer Center, Texas. Since irradiation may affect the immunogenicity of these mouse tumors [Chen et al. (1993) J. Immunol. 151:244–255], live cells or cell membranes prepared from these tumors are used for immunization. In some experiments these tumor cells are treated with IFN$_\gamma$ to upregulate Class II expression before use.

Studies have shown that the human B7.1 molecule can provide costimulatory signal for mouse lymphocytes [Murphy et al. (1994) J. Exp. Med. 180:223–231]. Due to this cross reactivity, it is possible to test the immunotherapeutic function of GPI-B7.1 in vivo in immunocompetent mice. Since antitumor immunity is tested by challenging the mice with wild type tumor cells (which lack human B7.1) the antibodies that might have been produced in mice against human B7.1 do not interfere assessing tumor protection studies. Mice are primed with tumor cells or tumor cell membrane equivalents. These tumor cells are either control, transfected, or reconstituted with GPI-B7.1. Some mice are repeatedly boosted with the appropriate tumor cell preparation at different intervals. After several weeks, the mice are challenged, subcutaneously or I.P., with untreated tumor cells in 0.2 ml saline. Mice are observed for growth of a solid tumor. When a tumor of 1–2 cm in size or an ulcerated tumor has developed, the mice are euthanized. Tumor size and mouse survival are compared between the control and experimental groups for up to 180 days. As controls, unreconstituted or mock transfected tumors are used. As a control for the effect of the reconstitution procedure, tumor membranes reconstituted with CD16B, a GPI-anchored Fc receptor are used [Nagarajan et al. (1995) supra; Selvaraj et al. (1988) Nature 333:565–567].

Tumor specific immunity is also determined by analyzing T cells in the spleen and other lymphoid organs of control and tumor immunized experimental mice. These lymphocyte preparations are used to assay for CTL activity and T cell proliferation. In triplicate $10^6$ responder cells (prepared by Histopaque isolation of lymphocytes from spleen) are cocultured with various amounts of irradiate stimulator cells (GPI-molecule positive or negative tumor cells) and incubated at 37° C. After several days 1) the cells are pulsed with 1 $\mu$Ci methyl-$^3$H-thymidine to assay cell proliferation; or the T cells are isolated from the wells and used in a $^{51}$Cr release assay to determine CTL activity against tumor targets.

Since we do not irradiate the cell membranes, the tumor cell membranes are prepared under sterile conditions for immunizations. GPI-B7.1 tumor but not control membranes, induce protective immunity against the parental tumor. It is possible that when cell membranes are injected they can be taken up by macrophages and presented to T cells to initiate the antitumor immune response. If membranes induce immunity by this mechanism, there could not be a significant difference between B7.1 positive or negative tumor cell membranes in inducing the antitumor immune response.

Like live tumor cells, the isolated cell membranes are not endowed with the capacity to produce cytokines or growth factors. Cytokines play an essential role in immune responses. Systemic administration of certain cytokines in tumor patients have shown to augment tumor specific immune responses and regression of tumors in some patients. Tumors transfected with cytokine genes induce potent antitumor immune responses and protective immunity.

Though cytokines such as GM-CSF, IFN$_\gamma$ and IL-2 have shown to be effective in inducing antitumor immune responses, we focus on IL-12 for the following reasons: IL-12 is a potent immunomodulatory cytokine [Trinchieri G. (1994) Blood 84(12), 4008–4027], induces differentiation of CTLs [Chouaib et al. (1994) Proc. Natl. Acad. Sci. USA 91, 12659–12663] and is 100–1,000 fold more effective than IL-2 in inducing T cell proliferation [Kubin et al. (1994) J. Exp. Med. 180, 211–222]. IL-12 synergizes with B7.1 in inducing T cell responses [Murphy et al. (1994) J. Exp. Med. 180:223–231; Kubin et al. (1994) J. Exp. Med. 180, 211–222]. The combination of B7.1 and IL-12 increases the longevity of the antitumor immune response [Chen et al (1995) Proc. Natl. Acad. Sci. USA 92, 247] and concentration of IL-12 as low as 1 ng when systemically administered, dramatically enhances the potency of a peptide vaccine against Meth A sarcoma. Therefore, the stimulating effect IL-12 (Pharmingen) has on the immune response induced by tumor cell membranes reconstituted with the GPI-B7.1 molecule is determined. The amount and doses of cytokine required for immunization are determined experimentally. Tumor membranes and cytokines are mixed and injected subcutaneously. Alternatively, cytokines are administered systemically [Noguchi et al. (1995) Proc. Natl. Acad. Sci. USA 92, 2219–2223] to mice immunized with tumor membranes. As controls, membranes and cytokines are injected separately. The dose of immunizations required is determined empirically for the type of tumor cells used. The influence of cytokine on the longevity of tumor specific immunity is determined. Mice immunized with GPI-molecule modified cell membranes are challenged with live parental tumors for different lengths of time to determine the longevity of the antitumor immune response induced by the immunization protocol. The effects of other cytokines are determined in conjunction with GPI-anchored fusion proteins and in conjunction with the GPI-anchor proteins and IL-12. A recent study [Gajewski et al. (1995) J. Immunol. 154, 5637–5648] shows that IL-12 and IL-6 cooperate with B7.1 in generation of antitumor CTLs in vitro. Therefore IL-12+IL-6 (available from Genzyme) combination is tested. Without wishing to be bound by theory, we believe these cytokines augment the antitumor immune response induced by GPI-B7.1 reconstituted tumor cell membranes.

In addition to B7.1, other adhesion molecules, such as B7.2, ICAM-1, ICAM-2, LFA-3, HSA and VCAM-1 (VCAM, vascular cell adhesion molecule) have been demonstrated to provide costimulation for various T cell responses [Liu et al. (1992) J. Exp. Med. 175, 437–445; Damle et al (1993) Cell Immunol. 148, 144–156; Damle et al (1992) J. Immunol. 148, 665–671; van Seventer, et al. (1991) J. Exp. Med. 174, 901–913]. CD40 and its ligand CD154 are also involved in the antitumor immune response [Mackey et al. (1997) Cancer Res. 57, 2569–2574]. B7-2, like B7.1, binds to CD28 and induces tumor rejection when expressed on tumor cells (Yang et al. (1995) J. Immunol. 154, 2794–2800) suggesting that B7.1 and B7.2 follow a similar mechanism to induce tumor rejection. However, the costimulatory signals provided by other adhesion molecules seem to be different from B7.1 and thus provide an additive effect. Crosslinking CD2 and CD28 with mAbs increases T cell responses compared to the ligation of either CD2 or CD28 alone [Pierres et al. (1988) Eur. J. Immunol. 18:685; Van Lier et al. (1988) Eur. J. Immunol. 18:167]. Expressing LFA-3 and B7.1 on an artificial APC augmented T cell responses to a superantigen [Parra eta al. (1994) *J. Immunol.* 153, 2479–2487]. These molecules cooperated to enhance cell adhesion, proliferation and cytokine production. In the murine system, costimulation by B7.1 and HSA synergizes CD4+ T cell proliferation [Liu et al. (1992) *Eur. J. Immunol.* 22, 2855–2859]. These costimulatory molecules not only work in concert to augment the same T cell responses, but, individually, stimulate T cells at different stages of activation [Damle et al. (1992) *J. Immunol.* 148, 1985–1992]. The introduction of various combinations of purified GPI-anchored molecules, by reconstitution, create the optimal target to facilitate various T cell regulatory and effector functions needed for tumor immunity. Our preliminary studies show that tumors expressing HS1A molecule induce expansion of tumor specific CTL responses in vivo [Wang et al. (1995) *Eur. J. Immunol.* 25:1163–1167]. Studies by Ananthaswamy and co-workers have shown that expression of ICAM-1 on K1735 melanoma cells induce tumor rejection. By converting these molecules to have GPI-anchors, the skilled artisan can prepare these individually or in conjunction with others, to determine the combination needed to create a highly immunogenic tumor cell or membrane preparation.

GPI-B7.1 with other costimulatory molecules such as GPI-ICAM-1 and HSA can further enhance immunogenicity. We have obtained a GPI-anchored ICAM-1 construct and expressed on CHO cells for purification. GPI-ICAM-1 is purified and reconstituted on the surfaces of K1735M2 cells. We have established CHO cell transfectants expressing HSA molecule. HSA is a naturally GPI-anchored molecule of about 30 amino acids. In nature it is expressed on B cells, activated T cells, monocytes, granulocytes, Langerhans cells and thymocytes. The HSA expressed on activated B cells has been shown to provide costimulatory signals for the induction of antigen-specific CD4+ T cell proliferation. HSA-specific mAb 20C8 can block T cell proliferation and can induce T cell anergy. We transfected HSA cDNA into the murine melanoma cell line K1735M2 and studies induction of T cell proliferation and cytotoxicity. Spleen cells from mice immunized with HSA-transfected K1735M2 showed enhanced T cell proliferation in a mixed lymphocyte tumor reaction assay and also displayed significant anti-tumor cytotoxicity to the parent tumor cell (K1735M2). This anti-tumor activity could be abrogated by pretreatment of effector cells with anti-mouse CD8+ mAb and complement. Under similar conditions spleen cells from C3H mice immunized with vector-transfected K1735M2 cells neither actively proliferated in a MLTR assay nor did they exert significant cytolytic activity to the respective tumor cell s in CTL assays. In summary our study demonstrated that HSA can provide a costimulatory signal for the T cell immune response against tumor cells in a murine model. Similar efficacy applies to the use of HSA in other mammalian systems, including but not limited to humans. HSA is purified by MAb affinity chromatography using M1/69 (hybridoma cells obtained from ATCC) coupled to Sepharose column and reconstitute them on K1735M2 cells. Tumor cells are reconstituted with one or a combination of different adhesion molecules, or unmodified.

In addition to the efficacy of GPI-B7.1 modified tumors in inducing tumor immunity in mice, these modified tumor cells or cell membranes can induce autologous antitumor CTL in humans in vitro. Initially, induction of T cell responses by reconstituted GPI-B7.1 are tested in human autologous and allogenic systems using the renal carcinoma cell line RCC-1 and the melanoma cell line SKMEL28. As shown in our preliminary studies, both of these cell lines induce T-cell proliferation upon B7.1 expression. Tumor cell lines are established from renal carcinoma and melanoma patients to test autologous T-cell responses to GPI-B7.1 reconstituted tumor cells. We use a similar method as the one used to establish human RCC-1 renal carcinoma cell line. Briefly, tumor tissue is rinsed with 300 $\mu$/ml of penicillin and 300 $\mu$g/ml of streptomycin, cut into small pieces of approximately 1 mm$^3$, then treated in a 15 ml centrifuge tube with 0.1% of collagenase in HBSS by shaking for 30 min. at room temperature. The fragments are allowed to settle for a few minutes and the cell suspension is transferred into new tube and collagenase activity neutralized with new cell culture media containing FBS. This collagenase treatment is repeated 3 times. Finally, the cell suspension is subjected to discontinuous (75% and 100%) gradient centrifugation. After a 30 min 450×g centrifugation, the enriched tumor cells on the top of 75% Histopaque layer are harvested, washed and cultured in a petri dish. Colonies of tumor cells are identified, differentiated from fibroblasts morphologically and isolated from the petri dish by localized trypsinization. The tumor cell line is maintained in DMEM supplied with 10% FBS.

FACS analysis is carried out to determine expression of MHC molecules and adhesion molecules. Tumors expressing the MHC Class I molecule are selected for further studies. Allogenic and autologous T cell proliferative response and CTL activity are tested after stimulation with untreated, B7.1 transfected and GPI-B7.1 reconstituted tumor cells or membrane preparations. Mononuclear cells (PBMC) are isolated from peripheral blood by 6% Dextran sedimentation and HISTOPAQUE™ 1077 gradient centrifugation. The PBMC are then used for stimulation assays or T cell separation. T cells are isolated by magnetic depletion of monocytes, B cells and NK cells after treatment with mAbs CLBFcgran-1 (anti-CD16), IV.3 (anti-CD32), and anti-CD19, followed by goat anti-mouse coated magnetic beads. T cells are separated by layering PBMC over a human T cell enrichment column (R & D Systems) and collecting the T cell enriched flow through. T cell preparations are >95% pure as seen by FACS for both methods.

For autologous stimulation by tumor cells, PBMC or purified T cells from the patient are incubated in a 96 well microtiter plate in complete RPMI 1640 containing 10% FBS as 2×10$^5$ cell/well. Irradiated (8,000 rads) tumor cells, either control, B7.1 transfected or reconstituted with 10–40 $\mu$g/ml of GPI-B7.1, or tumor membranes modified or unmodified with GPI-B7.1 are added to the PBL (peripheral blood lymphocytes) or PMBCs at different responder stimulator cell ratios. After three days, the MLTR cultures are left untreated or boosted with the same tumor cells, reconstituted, transfected or controls, and incubated for an additional 4 days. The cells are pulsed with 1 $\mu$Ci/well of [$^3$H]-thymidine for the last 18 hours of the incubation. The mean uptake of [$^3$H]-thymidine is determined by standard scintillation spectrometry and the standard deviation calculated of the triplicate cultures. As a control, allogenic stimulation is carried out in parallel as described above.

For in vitro generation of tumor specific CTL, effector autologous PBMC are primed by co-culturing these cells, for 8 days, with tumor cells or cell membranes (10:1) incorporated with GPI-B7.1. As a control untreated or B7.1 transfected tumors or membranes prepared from them are used as stimulators. The effector cells are recovered from bulk culture by HISTOPAQUE™ 1077 gradient centrifugation at 700×g for 20 minutes. After washing with medium, the cells are resuspended in culture medium and tumor specific CTL activity is measured standard chromium release assay. As a control target PHA-stimulated autologous lymphoblasts (PBMC stimulated with 10 μg/ml PHA (phytohemagglutinin) for 72 hours) are used. T lymphocytes are tested for their response to tumor membrane preparations with and without the reconstituted GPI-B7.1 molecule. Since a recent study [Gajeweski et al. (1995) *J. Immunol.* 154, 5637–5648] has shown that IL-12 and IL-6 can cooperate with B7.1 in augmenting the generation of antitumor CTLs in vitro we, in some experiments, include these cytokines during in vitro priming of CTL. The information obtained in this in vitro studies is used to expand tumor specific autologous CTLs in vitro for adoptive tumor immunotherapy or designing strategies for human tumor immunotherapy.

A prerequisite for success of the tumor immune response is the presence of immunogenic proteins and HLA (human histocompatability leukocyte antigen) class I MHC molecules in the tumor cells and the availability of surgically removed tumor specimens or available cell lines expressing desired cancer cell surface antigens. However, lack of expression of the HLA molecules can be overcome with the use of allogenic tumor cells or membranes or by the availability of tumor-specific antigens or peptides. The reconstitution of GPI-anchored receptors can also be applied to HLA molecules. It has been shown that both GPI-modified MHC HLA class I and class II molecules can bind specific peptides and induced T cells responses in vitro [Wettstein et al. (1991) *J. Exp. Med.* 174, 219–228; Huang et al. (1994) *Immunity* 1, 607–613].

We have described the creation of a functional GPI-anchored human B7.1 (GPI-B7.1) molecule that when incorporated into tumor cell membranes can stimulate an allogenic immune response, in vitro [McHugh et al. (1995) *Proc. Natl. Acad. Sci. USA* 92:8059-8063 and see herein]. Using the EG7 murine tumor system, we demonstrate that the incorporated GPI-B7.1 molecule can stimulate an anti-tumor immune response in vivo and increase the survival of mice after challenge with live tumor cells.

EG7 cells are derived from the murine T cell lymphoma EL4 that has been transfected with the cDNA for ovalbumin [Moore et al. (1988) *Cell* 54, 777–785]. This tumor cell line is used for several reason: EG7 cells are unable to stimulate a potent immune response in vivo, despite the expression of the foreign antigen, ovalbumin; the parental tumor, EL4, is immunogenic after modification with the B7-1 molecule [Chen et al. (1994) *Cancer Res.* 54, 5420–5423; Townsend et al. (1994) *Cancer Res.* 54, 6477–6483] and EG7 cells can be grown in large quantities for membrane preparation.

Figure 15A:
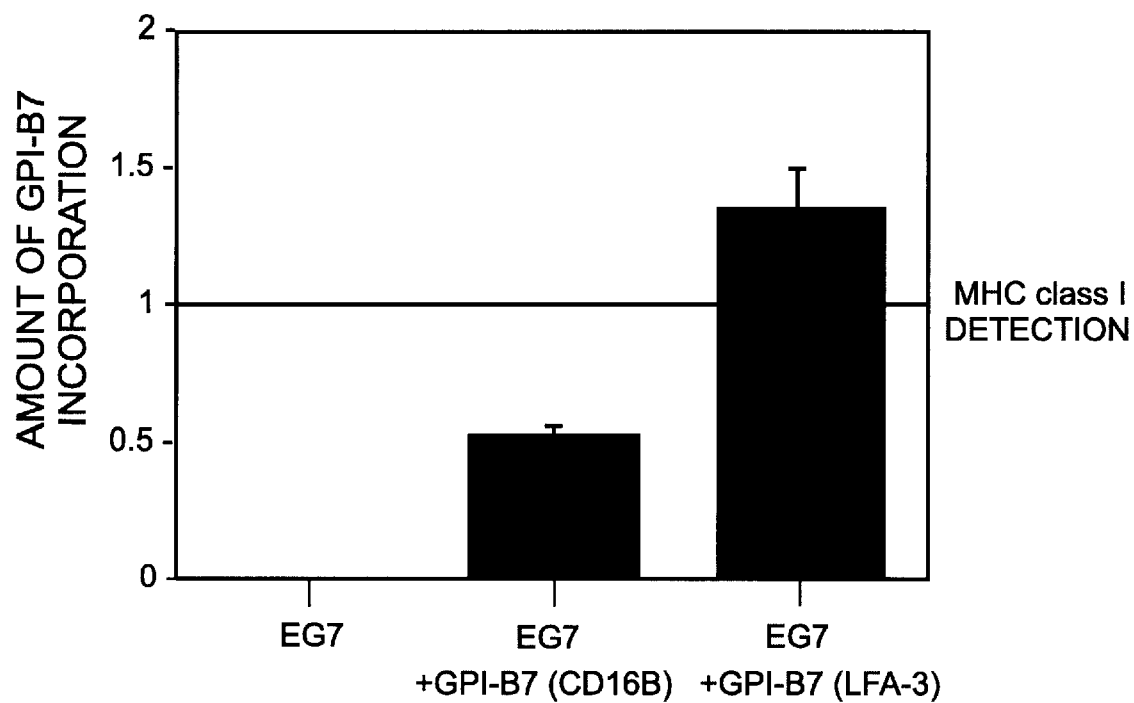
Figure 15B:
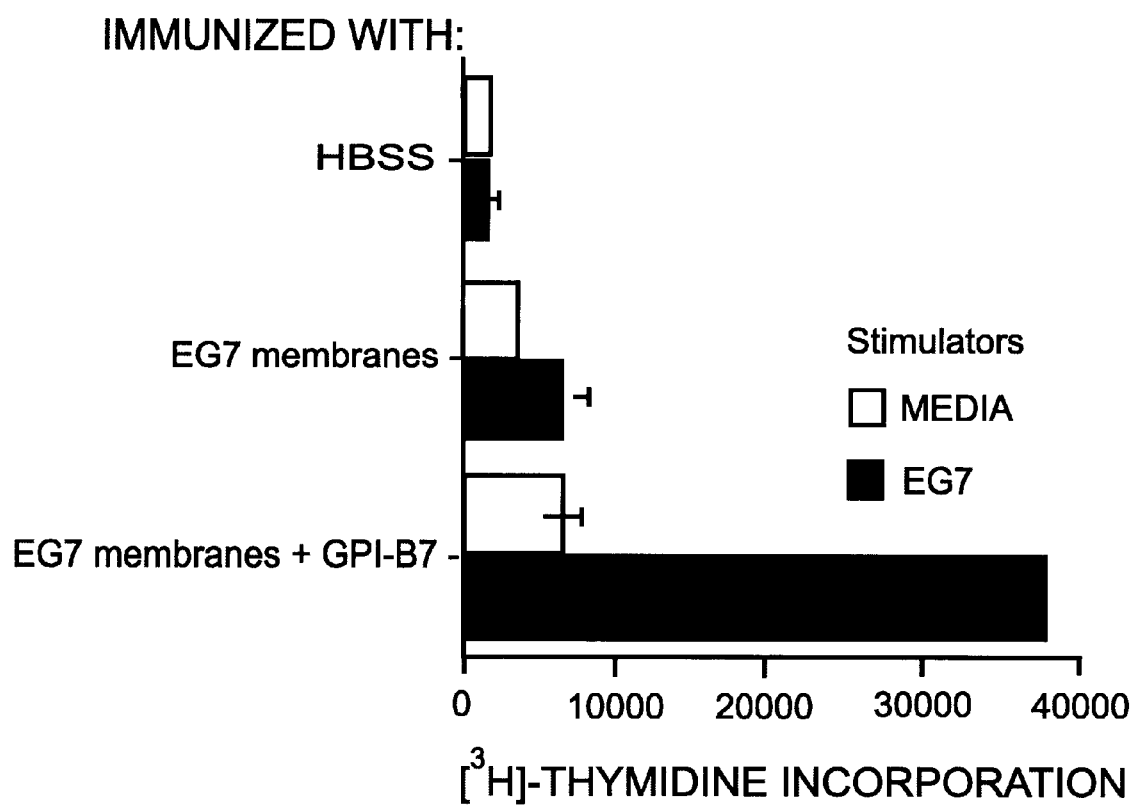

Cell membranes were prepared from EG7 cells [Maeda et al. (1983) *Biochem. Biophys. Acta* 731, 115] and modified to express GPI-B7.1. These membranes, when incubated for two hours with GPI-B7.1, incorporated a large amount of GPI-B7.1 (FIG. 15A). These reconstituted membranes were analyzed for B7.1 and class I expression and they were utilized to immunize mice. First, cellular proliferation of T cells from mice immunized, intraperitoneally, with the various membrane preparations was determined using a mixed lymphocyte tumor cell reaction assay. T cells from mice immunized with EG7 membranes that were modified with GPI-B7.1 proliferated when cocultured with EG7 cells. T cells from the HBSS control and EG7 membrane primed mice were unable to mount a significant proliferative response.

Figure 16A:
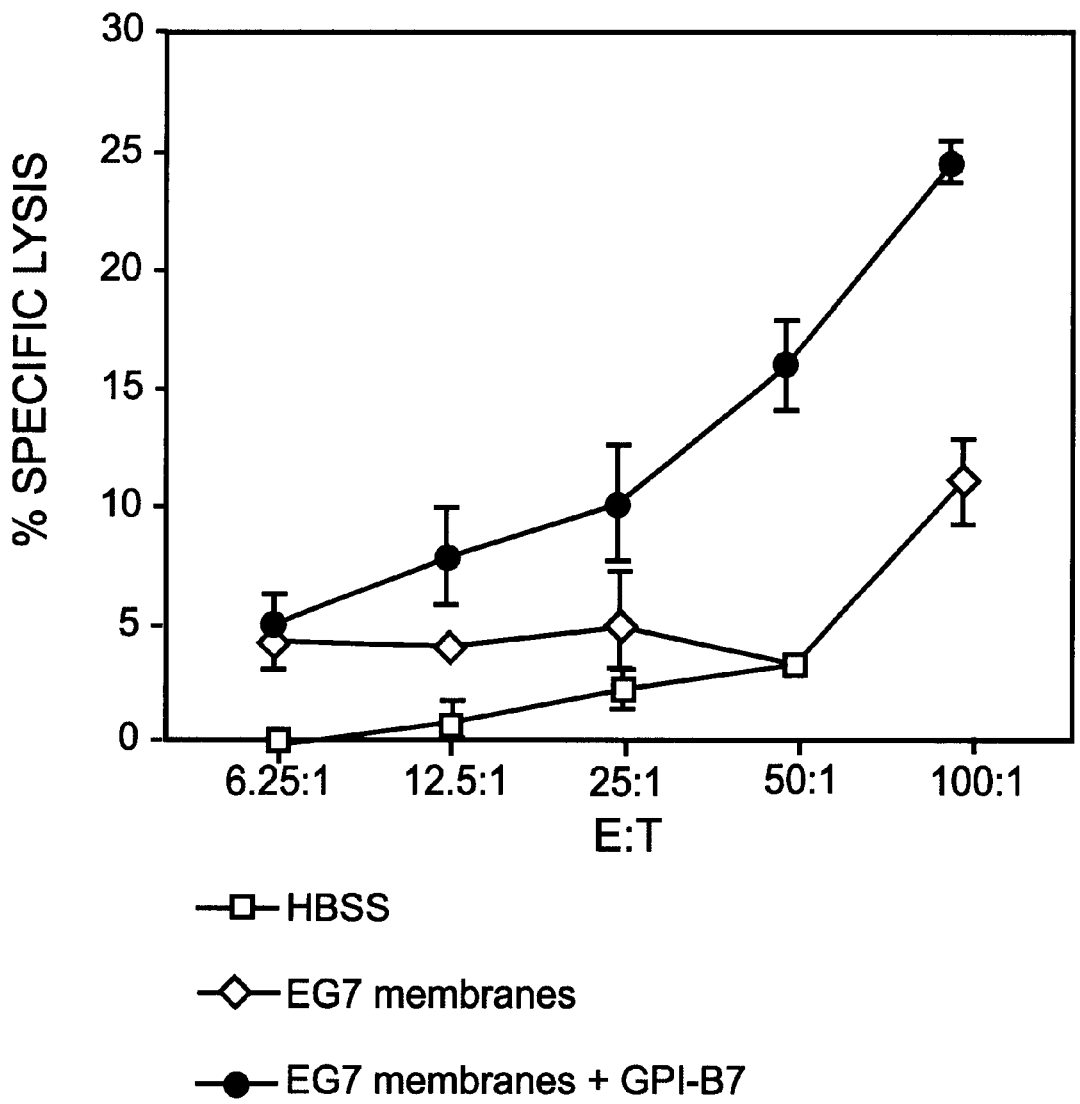
FIG. 16A provides a comparison of autologous T cell proliferation induced by B7.1 RCC-1 and GPI-B7.1 RCC-1 cells. T cells were obtained from patient's blood by passing the buffy coat through a nylon-wool column, followed by negative selection with anti-CD19 and anti-CD16 mAb coated magnetic beads. The resultant T cells ($1 \times 10^5$ cells/well) were cocultured with $2 \times 10^4$ irradiated tumor cells in a 96 well plate for 4 to 5 days. Each culture was pulsed with 1 mCi of [$^3$H]-TdR during the last 18 h, harvested, and counted using a beta counter.
Figure 16B:
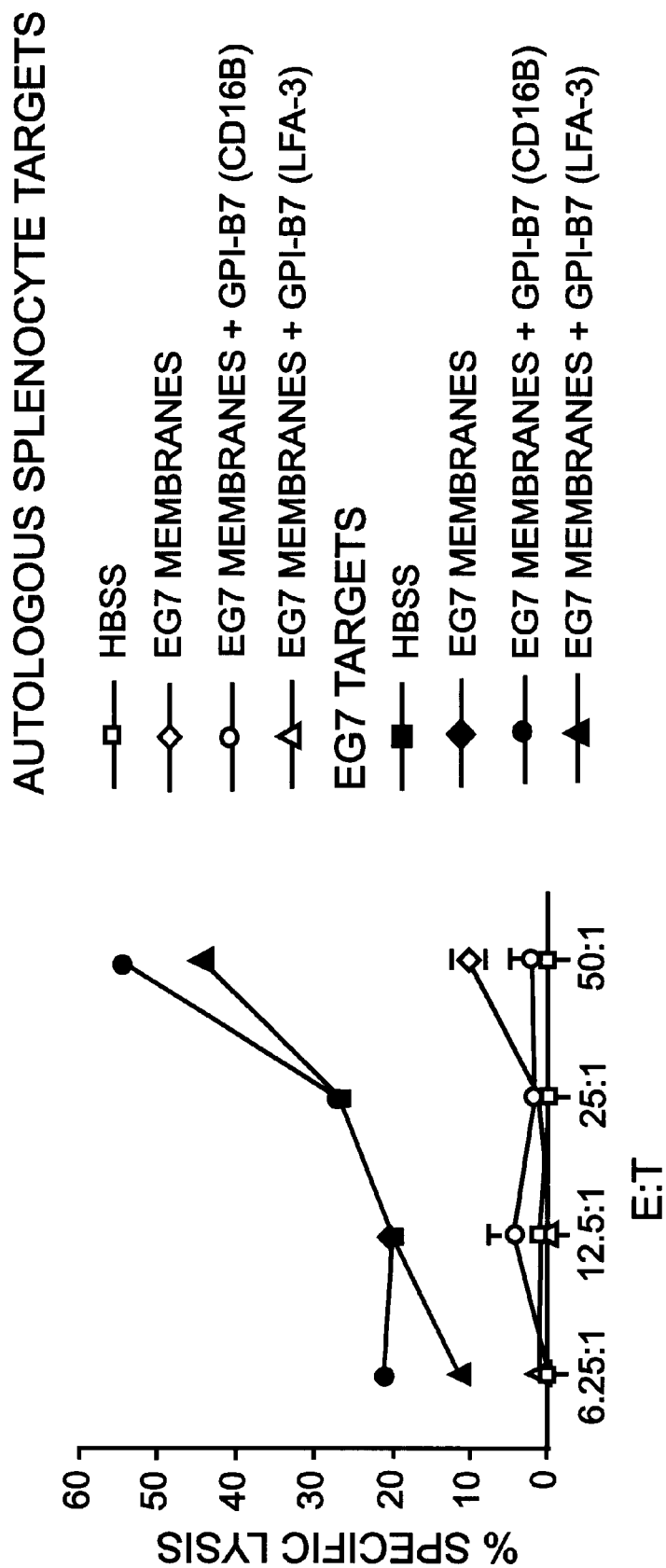
FIG. 16B shows that anti-B7 mAb blocks T cell proliferation induced by B7.1 and GPI-B7.1 transfected RCC-1. The MLTR assays were set up as described above. However, in the antibody blocking assay, the irradiated tumor cells were incubated with 5 $\mu$g/ml of anti-B7.1 mAb (aB7) for 30 min., mixed with responder cells and cultured for 4 to 5 days. Each culture was pulsed with 1 $\mu$Ci of [$^3$H]-TdR during the last 18 h, then harvested and counted using a beta counter.

Next, the generation of a CTL response against the parental tumor was demonstrated. After immunization, T cells were purified and restimulated in vitro with EG7 for 5 days, and then assayed for cytotoxicity to EG7 cells. In FIG. 16A, T cells from mice primed with EG7 membranes expressing GPI-B7.1 had an increased, although low, cytotoxic response to the EG7 targets, in comparison to the EG7 membrane or HBSS immunized controls. Without wishing to be bound by theory, membrane preparations are postulated to lack certain signals for T cell activation provided by live cells. To improve specific lysis of the EG7 targets, IL-12 was administered to the mice in multiple injections during the membrane immunizations. IL-12 has been reported to work in concert with B7.1 in generating strong CTL responses, as well as, tumor regression [Murphy et al. (1994) *J. Exp. Med.* 180, 223–231; Kubin et al (1994) *J. Exp. Med.* 180, 211–222; Gajewski et al. (1994) *J. Immunol.* 154, 5637–5648]. FIG. 16B shows that IL-12 treatment increased the specific lysis of the EG7 targets by the T cells primed with GPI-B7.1 reconstituted EG7 membranes, with little background lysis of autologous lymphocytes. The CTL activity in the absence of IL-12 treatment remained low. IL-12 treatment of mice immunized with HBSS or EG7 membranes did not enhance CTL activity. Mice immunized with EG7 membranes reconstituted with a different construct, B7.1 with the GPI tail from LFA-3 [Staunton et al. (1992) *J. Immunol.* 148, 3271–3274] was also included. This construct induced an immune response similar to that with the B7.1 molecule with the GPI tail from CD16B (FIG. 16B).

Figure 16C:
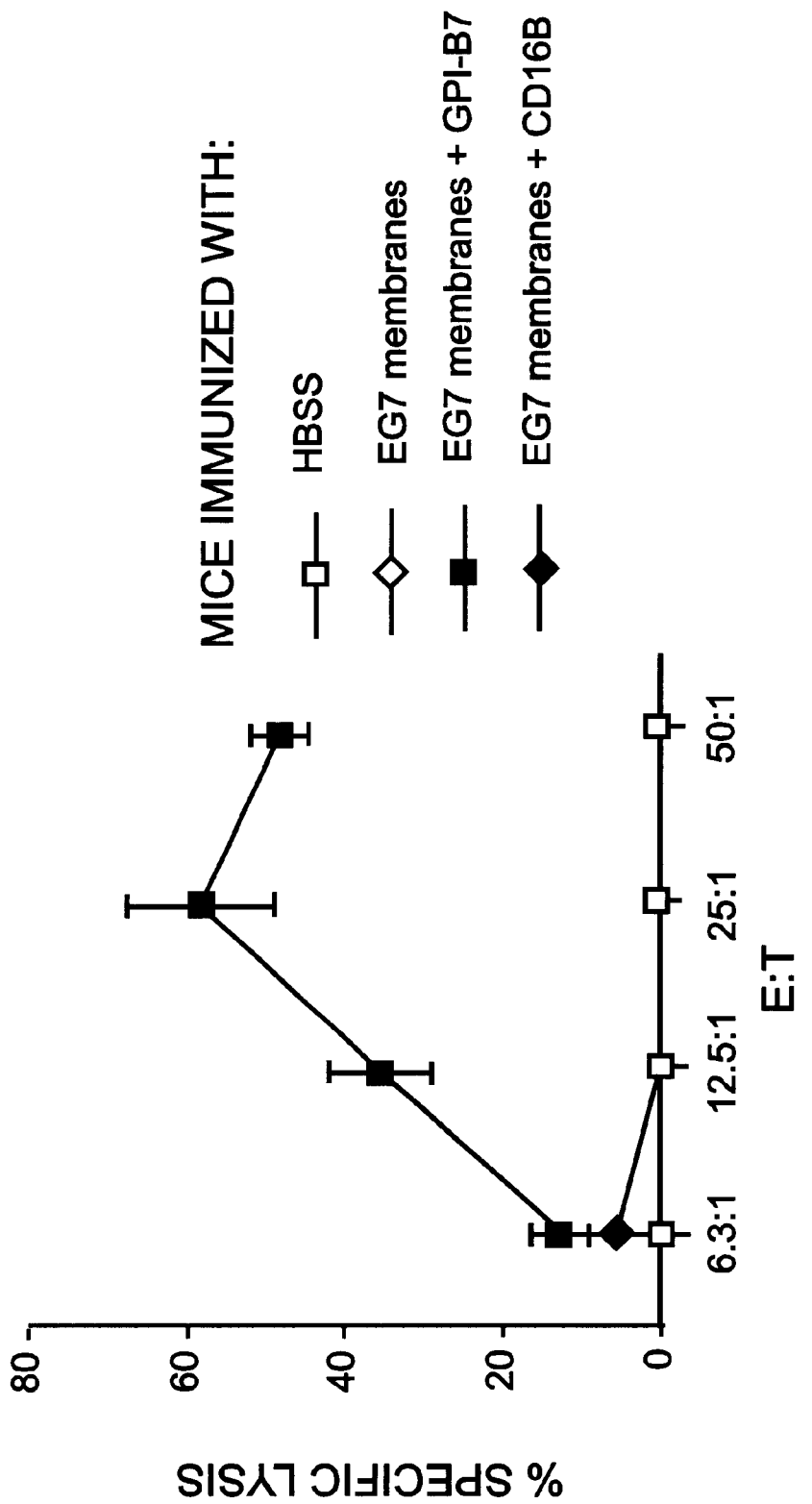
Figure 16D:
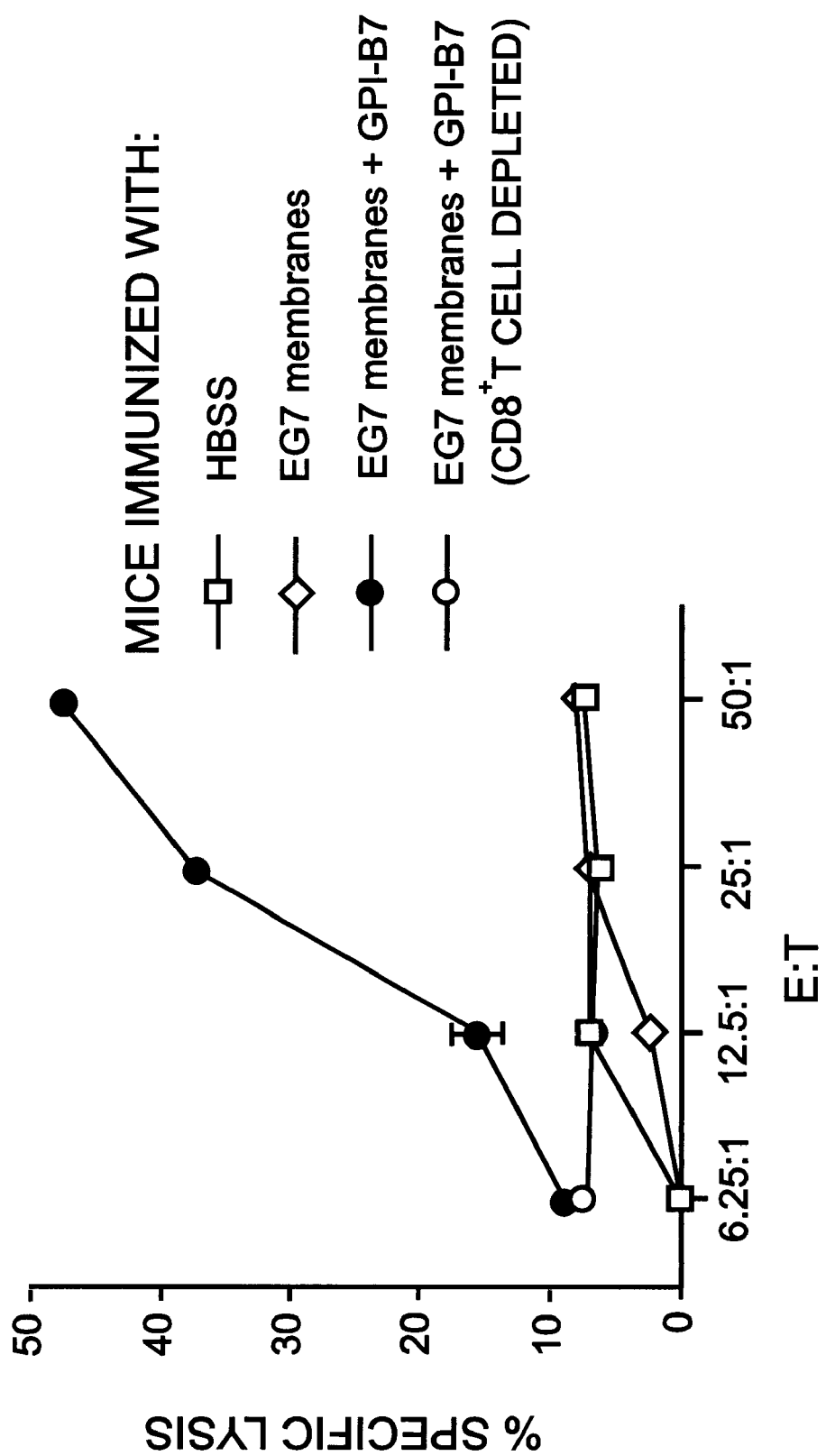

To eliminate the possibility that this method of incorporating lipid tails into tumor membranes was enough to stimulate T cells, tumor membranes incorporated with CD16B were included as a control. CTL responses of T cells from mice immunized with CD16B incorporated membranes were minimal in comparison to lytic activity measured from mice immunized with GPI-B7.1 incorporated membranes (FIG. 16C).

To investigate which cells might be the effectors of the anti-tumor cytotoxicity, CTL responses were analyzed after depletion of $CD3^+$ or $CD8^+$ T cells in vitro. The depletion of $CD3^+$ T cells from mice primed with GPI-B7.1 reconstituted membranes eliminated cytotoxicity, indicating that T cells and not NK cells were the effectors of the immune response to EG7 tumor cells. Removal of $CD8^+$ cells significantly reduced activity, indicating that $CD8^+$ T cells are the major effectors of the lytic activity toward the tumor cells. There was residual cytotoxicity (8%) which could be due to $CD4^+$ T cell activity or remaining $CD8^+$ T cells after complement lysis.

These results are consistent with the EG7 cell expression of class I, but not class II antigens, therefore only being recognized by $CD8^+$ T cells. In addition, some B7.1 expressing tumors have been shown to directly stimulate $CD8^+$ T cells without the help of $CD4^+$ T cells [Townsend and Allison (1993) *Science* 259, 368–370]. By expressing class I and B7.1, EG7 membranes may also be directly stimulating $CD8^+$ effector T cells.

Figure 17:
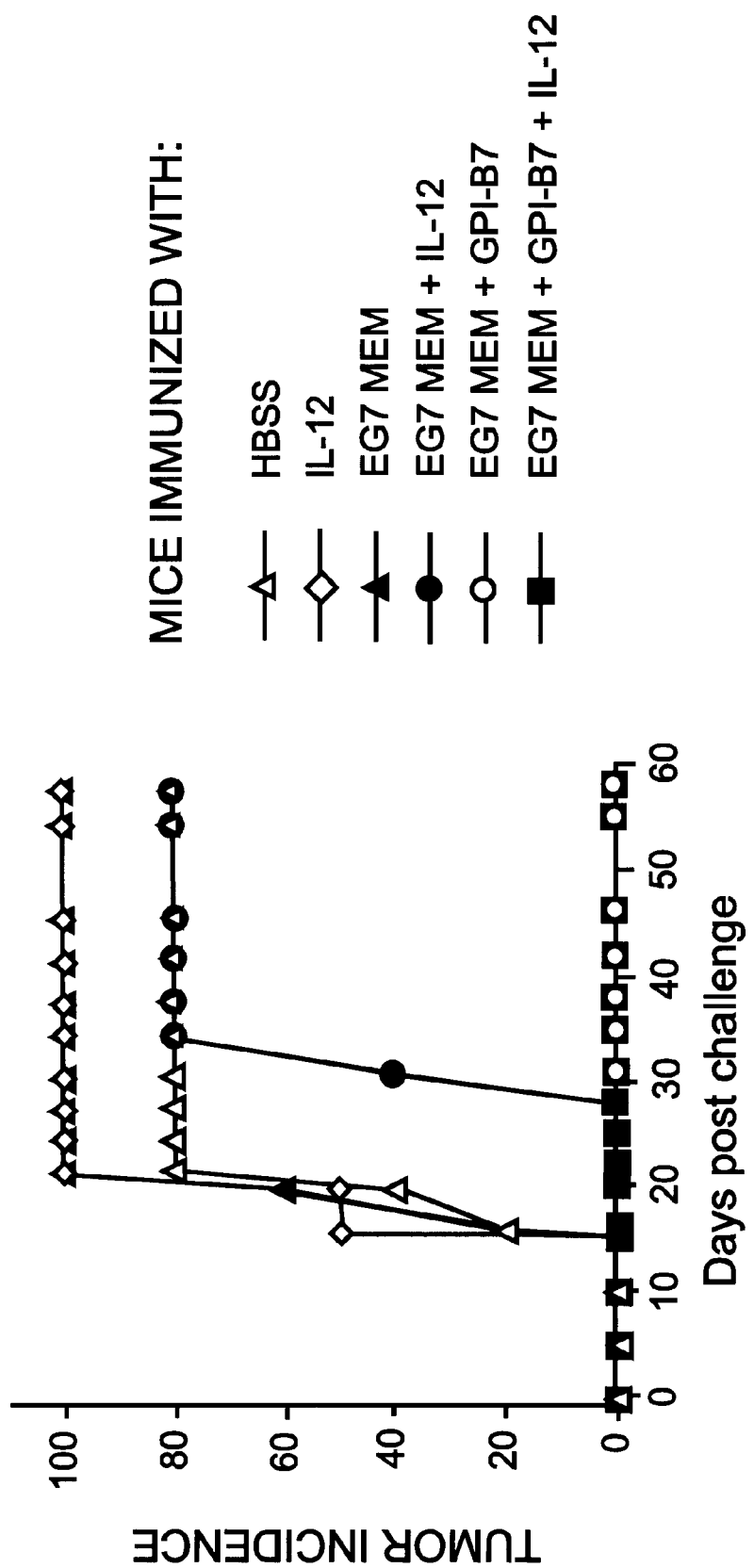
FIG. 17 demonstrates that immunization with GPI-B7 incorporated membranes provided protection from the parental tumor in vivo. Ten C57BL/6 mice were immunized with HBSS or 100 $\mu$g equivalent protein of EG7 membranes, with or without GPI-B7 incorporation, subcutaneously. Five mice in each group were given simultaneous injections of 2 ng rIL-12. After two weeks, the mice were boosted with the same material. One week later, mice were challenged subcutaneously with live EG7 cells. Mice were monitored every day for tumor incidence.
Figure 18:
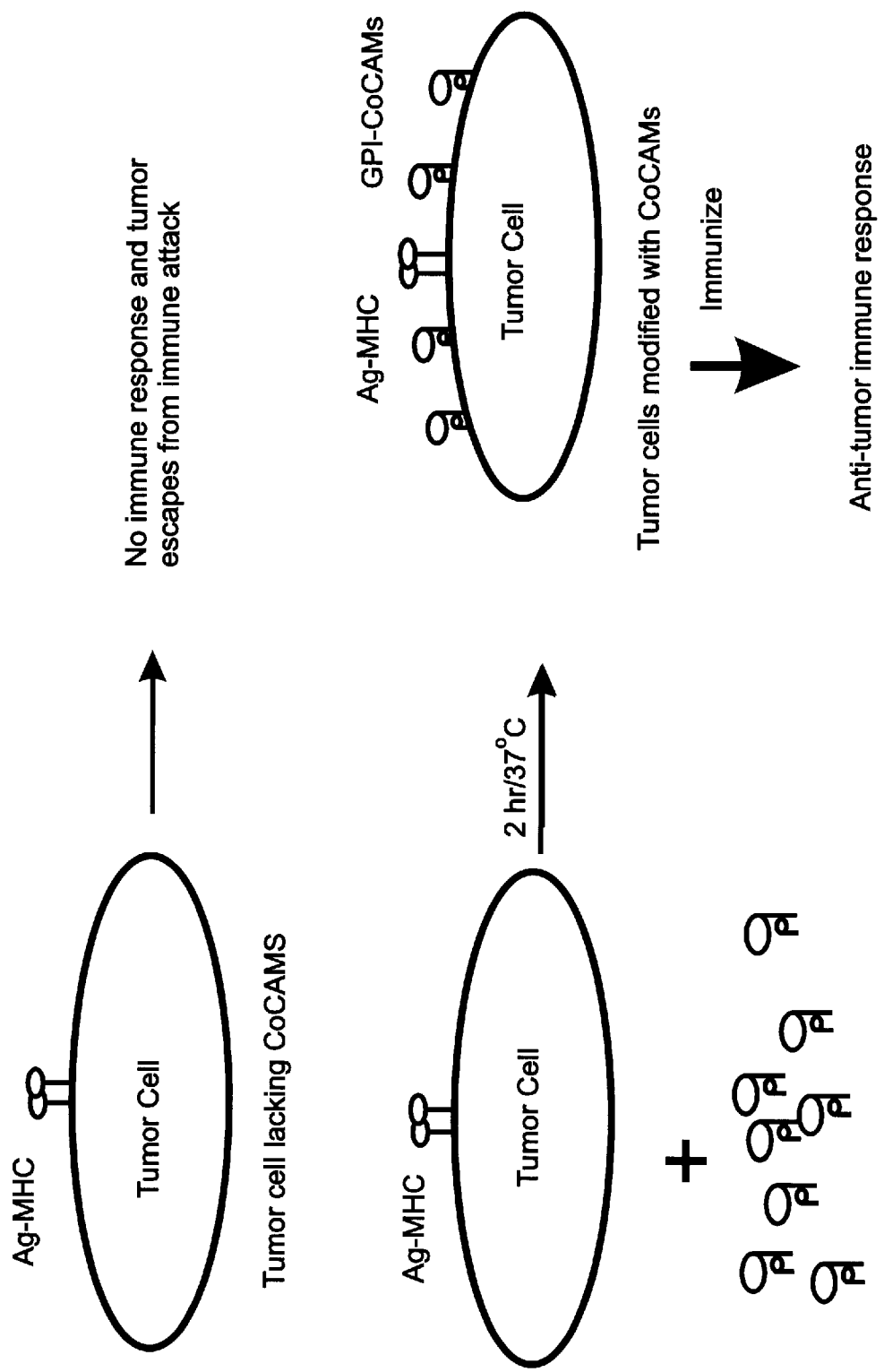

We have shown that EG7 membranes modified with GPI-B7.1 can generate CTL against the parental tumor, and we determined that these membrane preparations immunized mice against subsequent challenge to the parental tumor in vivo. Several mice were immunized twice subcutaneously with GPI-B7.1 modified or untreated membranes in the presence or absence of 2 ng IL-12. One week after the final immunization, mice were challenged subcutaneously with live EG7 cells. After a few weeks, tumors developed and grew rapidly in mice immunized with HBSS, IL-12, or EG7 membranes (FIG. 17). However, mice immunized with EG7 membranes modified with GPI-B7.1, with or without IL-12, remained tumor free for over 80 days. Mice were protected from tumor growth by immunization with GPI-B7.1 incorporated EG7 membranes without IL-12 treatment, indicating that the low CTL activity measured in vitro is sufficient for tumor rejection in vivo. It is also possible that the subcutaneous site of immunization for the tumor protection studies is a more efficient route for induction of anti-tumor immunity than the intraperitoneal route. If so, IL-12 treatment may not be as critical as the immunization route to induce a tumor specific immune response.

Although there was a delay in tumor growth, tumors grew in mice immunized with EG7 membranes and IL-12 (FIG. 17). Without wishing to be bound by theory, it is postulated that IL-12 treatment enhances immune activity to EG7 membranes. Perhaps macrophages were being activated, ingesting the membrane particles and subsequently presenting the antigens to $CD4^+$ T cells. $CD4^+$ T cells may secrete cytokines that costimulate tumor specific $CD8^+$ CTL that are recognizing B7-deficient tumor cells. Tumors still developed, however, indicating that this method of immunization was not sufficient to induce a long term effector or memory response. As summarized in Table 1, only mice immunized with GPI-B7 modified membranes are protected from tumor challenge. Mice immunized with EG7 membranes, with or without IL-12, still grow tumors. This indicates that indirect presentation of tumor antigens by APC or bystander help is not efficient in inducing protective immunity.

Exogenous GPI-anchored B7.1 molecule is added to the membrane preparation, and therefore it cannot be shed or replaced after cell division, internalization, or shedding. Expression on live cells, by contrast, is lost rather quickly. Live tumor cells, however, would never be administered to human patients. Other preparations of tumor cells (non-viable) need to be employed, such as irradiated cells or cell membrane preparations. However, irradiated tumor cells may also cause problems, if not all the tumor cells have been killed by irradiation. In addition, some murine tumor cells when irradiated are unable to induce a potent immune response to the parental tumor [Guo et al. (1994) supra; Townsend and Allison (1994) supra].

As an alternative, we have employed isolated tumor cell membranes. These preparations are advantageous in that they do not divide or have the metabolic functions of intact, living cells. As shown by ELISA comparing freshly reconstituted membranes and those assayed after 4 days, GPI-B7.1 is expressed at a similar level. Membrane preparations also retain the ability to stimulate cells in culture. In many studies, T helper cell membranes are seen to stimulate B cells in vitro [Brian, A. A. (1988) Proc. Natl. Acad. Sci. USA 85, 564–568; Hodgkin et al. (1991) J. Immunol. 147, 3696–3702]. In addition, membranes of CHO cells expressing GPI-B7.1 polyclonally stimulate T cells in the presence of phorbol 12'-myristate-13-acetate (PMA). Membranes can also be easily stored in frozen aliquots that can be quickly incorporated with GPI-anchored proteins. To our knowledge, this is the first technique shown to express new proteins on isolated membrane preparations. These membranes provide a stable environment for GPI-anchored molecules.

These studies indicate that protein transfer of GPI-modified costimulatory molecules is an alternative to gene transfer for tumor immunotherapy. Gene transfer may present problems for human tumor immunotherapy in the clinical setting. This method introduces foreign vectors, some of viral origin. At sites of incorporation, these vectors could introduce chromosomal mutations. As well, due to the immunity developed against vaccinia viral proteins, the vaccinia-based vectors can be used only once to deliver the desired genes [Ada, G. L. (1993) Fundamental Immunology (ed. Paul, W. E.) Vol. 768, 1309–1352. Raven Press, Ltd., New York]. Other viral vectors, such as adenovirus, also increase cellular infiltration at the site of delivery, indicating an immune response to the vector, that would prevent subsequent use for gene therapy [Nabel et al. (1992) Medical Sci. 89, 5157–5161; Davis et al. (1993) Hum. Gene Ther. 4, 733–740]. The incorporation (by protein transfer) of the GPI-anchored proteins which stimulate protective cellular immune response(s) has the further advantage over incorporation via recombinant expression that tumor cell membranes, which in nature lack a B7 or equivalent cell surface immune modulator, can be prepared from surgically excised tumor tissue without an intermediate step of tumor cell propagation in vitro. We have demonstrated that the GPI-anchored B7.1 molecule incorporated on the tumor cell is able to deliver a costimulatory signal to tumor specific T cells in vivo. Moreover, it is possible to incorporate GPI-anchored molecules onto primary tumor cells, which has proven difficult with gene transfer. Protein transfer also allows for the expression of myriad GPI-anchored molecules at one time. This method can eliminate the problems associated with gene transfer using foreign vectors and allow functional expression of B7.1 or other molecules in a matter of hours.

The subject GPI-CoCAM-modified compositions and methods can be used for treating any vertebrate host that may has or is subject to transformation of cells resulting in neoplasia. The subject compositions may be used with mammals, e.g. equines, bovines, canines, felines, rodents, and the like, particularly primates, and more particularly humans.

The compositions and methods of the present invention can be used to prevent and/or treat by stimulating a cytotoxic immune response to any neoplastic or tumorous condition in which the tumor cells fail to express cell surface B7 or other immunostimulatory molecules, including but not limited to, carcinomas, melanomas, sarcomas, leukemias, lymphomas, where the tissues involved may be the prostate, mammary, neuronal, testes, lung, cutaneous tissue, lymph node, mucosal tissue, muscle tissue, lymphocytes, ovary, glandular, e.g. pancreas, and the like. The subject compositions may be used with hyperproliferative tissue, precancerous but neoplastic lesions, a single tumor, or metastatic tumors.

Immunogenic carriers may be used to enhance the costimulatory effect of the tumor cells, irradiated tumor cells or tumor cell membranes, wherein at lest one GPI-anchored surface molecule, preferably B7.1, and potentially including or further including one or more of the following: ICAM-1, HSA, B7.2, CD40 and CD154 among others, incorporated into the membranes within each of the foregoing preparations. Such carriers include but are not limited to proteins and polysaccharides, liposomes, microspheres and bacterial cells and membranes.

The art knows how to administer immunogenic and/or immunotherapeutic compositions so as to generate a protective and/or therapeutic immune response, preferably a cell-mediated immune response, to prevent the establishment of a tumor and/or to result in regression of a previously established tumor.

The immunotherapeutic compositions of the present invention may be formulated by any of the means known in the art. Such vaccines are typically prepared as injectables, either as suspensions or emulsions. Solid forms suitable for emulsification or suspension in liquid prior to injection may also be prepared.

The active immunotherapeutic ingredients of the present invention are often mixed with excipients or carriers which are pharmaceutically acceptable and compatible with the GPI-B7.1-modified tumor cells, UV-irradiated tumor cells or tumor cell membranes. Suitable excipients include but are not limited to water, saline, dextrose, glycerol, ethanol, or the like and combinations thereof. The concentration of the immunogenic polypeptide in injectable formulations is usually in the range of 0.2 to 5 mg/ml.

In addition, if desired, the present immunotherapeutic compositions may contain minor amounts of auxiliary substances such as wetting or emulsifying agents, pH buffering agents, and/or adjuvants which enhance the effectiveness of the vaccine.

The immunotherapeutic compositions of the present invention may be formulated by any of the means known in the art. Such vaccines are typically prepared as injectables, either as suspensions or emulsions. Solid forms suitable for emulsification or suspension in liquid prior to injection may also be prepared.

The active immunotherapeutic ingredients of the present invention are often mixed with excipients or carriers which are pharmaceutically acceptable and compatible with the GPI-B7–1-modified tumor cells, UV-irradiated tumor cells or tumor cell membranes. Suitable excipients include but are not limited to water, saline, dextrose, glycerol, ethanol, or the like and combinations thereof. The concentration of the immunogenic polypeptide in injectable formulations is usually in the range of 0.2 to 5 mg/ml.

In addition, if desired, the present immunotherapeutic compositions may contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide; N-acetyl-muramyl-L-threonyl-D-isoglutamine (thr-MDP); N-acetyl-nor-muramyl-L-alanyl-D-isoglutamine (CGP 11637, referred to as nor-MDP); N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE); and RIBI, which contains three components extracted from bacteria, monophosphoryl lipid A, trehalose dimycolate and cell wall skeleton (MPL+ TDM+CWS) in a 2% squalene/Tween 80 emulsion. The effectiveness of an adjuvant is measured, for example, by determining the extent of a cytotoxic immune response specific for the tumor cell at tissue, by measuring T cell activation and/or proliferation, resulting from administration of the GPI-B7–1-modified tumor cells or membranes vaccines which are also contain the various adjuvants. Such additional formulations and modes of administration are known in the art and can also be used.

Pharmaceutically acceptable salts for formulation within the immunotherapeutic compositions of the present invention include, but are not limited to, the acid addition salts (formed with free amino groups of the GPI-anchored fusion protein or other free amino acid groups associated with the cells or membranes) which are formed with inorganic acids, e.g., hydrochloric acid or phosphoric acids; and organic acids, e.g., acetic, oxalic, tartaric, or maleic acid. Salts formed with the free carboxyl groups of the immunogenic preparation may also be derived from inorganic bases, e.g., sodium, potassium, ammonium, calcium, or ferric hydroxides, and organic bases, e.g., isopropylamine, trimethylamine, 2-ethylamino-ethanol, histidine, and procaine.

The immunotherapeutic compositions of the present invention are administered in a manner compatible with the dosage and formulation, and in such amount as will be prophylactically and/or therapeutically effective. The quantity to be administered, which is generally in the range of about 100 to 5,000 µg of protein per dose, depends on the subject to be treated, the capacity of the individual's immune system to generate a cytotoxic immune response, and the degree of protection or cytotoxic response desired. Precise amounts of the costimulatory ingredient required to be administered may depend on the judgment of the physician and may be peculiar to each individual, but such a determination is within the skill of such a practitioner.

The vaccine or other immunotherapeutic composition may be given in a single dose or multiple dose schedule. A multiple dose schedule is one in which a primary course of treatment (or vaccination) may include 1 to 10 or more separate doses, followed by other doses administered at subsequent time intervals as required to maintain and or reinforce the cytotoxic immune response, e.g., at 1 to 4 months for a second dose, and if needed, a subsequent dose(s) after several months.

While it is possible to inject the GPI/B7 (alone or in combination with other GPI-modified costimulatory factors and/or cytokines, e.g., interleukin-12) into a tumor in a patient or animal, it is preferred to prepare irradiated tumor cells or cell membranes into which the GPI-B7 fusion protein, or irradiated tumor cells or membranes into which GPI-B7-1 plus one or more additional GPI-modified costimulatory factors and/or cytokine (such as IL-12) and incorporate those preparations into immunotherapeutic compositions for administration to the patient or animal.

Liposomes are not a preferred way of introducing a GPI-anchor-containing fusion protein into cell surfaces because there is a tendency for the fusion protein to remain associated with the liposome and not become incorporated into cell membranes such as the target tumor cell membranes contemplated in the present invention.

The human B7-1 coding and amino acid sequences are presented in Genbank, Accession No. M27533 and mouse B7-1 is available under Genbank Accession No. X60958; see also Freeman et al. (1989) *J. Immunol.* 143, 2714–2722. The B7-2 coding and amino acid sequences are disclosed in WO 95/03408 (published February 1995) in the Sequence Listing. The HSA coding sequences are disclosed in Kay et al. (1990) *J. Immunol.* 145, 1952–1959. Interleukin-12 is described by Hollander et al. (1988) *J. Immunol.* 141, 4283–4290. The nucleotide sequence and deduced amino acid sequence of LFA-3 is disclosed in FIG. 4 of U.S. Pat. No. 5,506,126 (Seed and Aruffo, filed Oct. 18, 1993). The decay accelerating factor GPI anchor coding sequence is disclosed in Caras et al. (1987) *Science* 238, 1280–1283, see also Tykocinski et al. (1995) *Proc. Natl. Acad. Sci. USA* 92,3555–3559.

Monoclonal or polyclonal antibodies, preferably monoclonal, specifically reacting with a B7-1/GPI fusion protein of the present invention may be made by methods known in the art. See, e.g., Harlow and Lane (1988) *Antibodies: A Laboratory Manual,* Cold Spring Harbor Laboratories; Goding (1986) *Monoclonal Antibodies: Principles and Practice,* 2d ed., Academic Press, New York.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning,* Second Edition, Cold Spring Harbor Laboratory, Plainview, New York; Maniatis et al. (1982) *Molecular Cloning,* Cold Spring Harbor Laboratory, Plainview, N.Y.; Wu (ed.) (1993) *Meth. Enzymol.* 218, Part I; Wu (ed.) (1979) *Meth Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics,* Cold Spring Harbor Laboratory, Cold Spring Harbor, N.Y.; Old and Primrose (1981) *Principles of Gene Manipulation,* University of California Press, Berkeley; Schleif and Wensink (1982) *Practical Methods in Molecular Biology;* Glover (ed.) (1985) *DNA Cloning* Vol. I and II, IRL Press, Oxford, UK; Hames and Higgins (eds.) (1985) *Nucleic Acid Hybridization,* IRL Press, Oxford, UK; and Setlow and Hollaender (1979) *Genetic Engineering: Principles and Methods,* Vols. 1–4, Plenum Press, New York. Abbreviations and nomenclature, where employed, are deemed standard in the field and commonly used in professional journals such as those cited herein.

All references cited herein are hereby incorporated by reference in their entirety.

The following examples are provided for illustrative purposes, and is not intended to limit the scope of the invention as claimed herein. Any variations in the exemplified articles which occur to the skilled artisan are intended to fall within the scope of the present invention.

EXAMPLES

Example 1

Cell Lines

The mouse melanoma K1735 (generously provided by I. Fidler, Anderson Cancer Center, Houston), Chinese hamster ovary (CHO) cell line K1, human breast cell carcinoma T47D, human T-cell leukemia Jurkat, human Burkitt lymphoma Ramos, human lymphoblastic leukemia MOLT4 (American Type Culture Collection, ATCC, Rockville, Md.), and T-cell lymphoma SKW3 were cultured in complete RPM1 medium 1640 (HyClone) containing 10% bovine calf serum (BCS, HyClone). The human melanoma cell lines WM115 and SKMEL28 (ATCC) were maintained in Dulbecco's modified Eagle's medium (DMEM) with 10% BCS containing 2 mM L-glutamine and 1 mM each nonessential amino acid. CHO CD16B cells were cultured in complete RPM1 medium 1640 with 10% BCS supplemented with hygromycin B (Calbiochem, San Diego, Calif.) at 200 µg/ml.

Example 2

Monoclonal Antibodies

The MAbs used were anti-human B7 (L307.4, mouse IgG1 α, Becton Dickinson, San Jose, Calif.); anti-mouse B7 (1G10, rat IgG2a, PharMingen, San Diego, Calif.); anti-CD16 (FcγRIII) [C1,B Fegran-1, mouse IgG2a, (SelvaRaj et al. (1988) *Nature* 333, 565–567)]; anti-CD32 (FcγRII) (IV.3, mouse IgG2b, ATCC); anti-CD19 (4G7 mouse IgG1 α, Becton Dickinson, San Jose, Calif.); and P3X63, a myeloma IgG1, used as a negative control antibody.

Example 3

Plasmid Construction and Cell Transfection

A DNA fragment encoding the first 243 amino acids of human B7-1 was amplified by PCR from the pT7 vector (A. Ansari, Emory University, Atlanta). The sense primer (5'-CCCTAAGCTTCTGAAGCCATGGGC-3') (SEQ ID NO:1) consists of an oligonucleotide corresponding to nucleotides 300–323, including the 5' signal sequence and initiation codon of human B7-1 with a modification to include a HindIII restriction site (underlined). The antisense primer (5'-CAATTGATCAGGAAAATGCTCTTGCTT-3') (SEQ ID NO:2) corresponds to nucleotides 1020–1043 of human B7-1 with the introduction of a Bcl I site (underlined) and a three nucleotide overhand complementary to the 5' end of the CD16B PCR product (boldface). This modification to create the Bcl I site at the B7-1 and CD16B joining site resulted in a conservative amino acid change from Leu to Val. The DNA fragment encoding the signal for GPI-anchor attachment of CD16B was amplified by PCR from a cDNA vector [Kuroski and Ravetch (1989) *Nature* 342, 805–807; Lanier et al. (1989) *Science* 246, 1611–1613]. The sense primer (5'-CCTGATCAATTGGCAGTGTCAACCATCTCA-3') (SEQ ID NO:3) corresponds to nucleotides 678–698 and contains 12-nucleotide overhang (boldface) at the 5' end complementary to the 3' end of the amplified B7-1 PCR product which contains the Bcl I site (underlined). The antisense primer (5'TCTTCTAGAGCTTCAAATGTTTGTCTTCACAGA-3') (SEQ ID NO:4) corresponds to nucleotides 780–812 of CD16B and contains an Xba I restriction site (underlined). The GPI anchor region from CD16B incorporated in the GPI/B7-1 fusion protein encompasses amino acids 193–234 of CD16B. The two amplified gene sequences were annealed to form a chimeric GPI-anchored B7-1 molecule by the overlap PCR method [Horton et al. (1989) *Gene* 77, 61–68] using 0.5 µg each of the B7-1 sense and CD16B antisense primers. The resulting chimera was cloned in the shuttle vector TA (Invitrogen, San Diego, Calif.), amplified in *Escherichia coli* DH5α and then subcloned in the neomycin-resistance plasmid pCDNA3 (Invitrogen, San Diego, Calif.), using the new flanking restriction sites. All end products were sequenced to be sure no further mutations had occurred as the result of the PCR manipulations. Representative structures resulting from overlapping PCR are shown in FIG. 11.

The chimeric gene was subcloned into the eukaryotic expression vector pCDNA3neo, and the resultant recombinant plasmid was transfected into CHO K1 cells by using the $CuCl_2$ precipitation method [Chen and Okayama (1987) *Mol. Cell. Biol.* 7, 2745–2752], and transfectants were selected with G418 (GIBCO/BRL) at 800 µg/ml. The chimeric B7-1+ CHO cells have been maintained in RPM1 1640/10% BCS supplemented with G418 at 400 µg/ml.

Phosphatidylinositol-specific phospholipase C (PIPLC) treatment was carried out to confirm that the B7-1 moiety was anchored to the cell surface by a GPI anchor. Recombinant CHO cells were treated with 0.2 U/ml of PIPLC for 1 hr at 37° C., and the release of GPI-anchored molecules was monitored by fluorescence-activated cell sorting. Nearly 99% of the surface expression of the fusion protein was reduced by PIPLC treatment (See FIG. 4).

Flow cytometry analysis confirmed expression of the fusion protein on the cell surface; this analysis was performed as previously described (Selvaraj et al. (1988) supra).

Example 4

Immunoaffinity Purification of GPI-B7

To prepare the anti-human B7-1 mAb affinity column and ovalbumin precolumn, CNBr-activated Sepharose 4B (Pharmacia, Piscataway, N.J.) was swollen in 1 mM HCl and coupled to anti-human B7 mAb an ovalbumin according to the manufacturer's instructions.

Ten grams of CHO GPI-B7 cells were lysed with 50 ml of 50 mM octyl β-glucoside in 50 mM Tris-HCl, pH 8.0, containing 5 mM iodoacetamide, 1 mM phenylmethanesulfonyl fluoride, and 1% aprotinin overnight at 4° C. The lysate was ultracentrifuged at 93,000×g for 1 h and sequentially passed overnight through the ovalbumin-coupled precolumn and the 1-ml anti-human B7 mAb-coupled column. The affinity column was washed with the following: (i) 50 ml of 50 mM Tris-HCl, pH 8.0, with 200 mM NaCl and 1% Triton X-100, (ii) 25 ml of 20 mM triethylamine, pH 10.5, with 1% octyl β-glucoside, and (iii) 10 ml of 50 mM Tris-HCl, pH 8.0, containing 1% octyl β-glucoside. Onemilliliter fractions were eluted with 50 mM glycine-HCl, pH 3.0, with 200 mM NaCl and 1% octyl β-glucoside, immediately neutralized with 1 M Tris-HCl, pH 9.0, and analyzed for B7-1 by ELISA. Purity of GPI-B7 was determined by silver staining and Western blotting (ECL kit, Amersham, Arlington Heights, Ill.) of the fractions after SDS/PAGE. Selected fractions were pooled and passed through Centricon-30 filters (Amicon, Beverly, Mass.) for concentration and removal of detergent octyl glucoside. The yield in the concentrated fraction is about 200–400 μg as determined by the DC (detergent-compatible) protein assay (Bio-Rad Laboratories, Hercules, Calif.).

Example 5
Cell Binding Assays

Microtiter plates were precoated, in triplicate, with either elution buffer or purified GPI-B7 at 10 μg/ml for 1 h at room temperature, and then blocked with DMEM/10% BCS. To some wells, anti-human or anti-mouse B7-1 mAb was added at 5 μg/ml and incubated for 30 min at room temperature. Without removing the antibodies, 200 μl of $^{51}$Cr-labeled cells resuspended to $2.5 \times 10^6$ cells per ml in binding buffer [2% IgG-low fetal bovine serum (FBS) (GIBCO) in phosphate-buffered saline (PBS) with 5 mM EDTA] were added and the wells were filled to capacity with binding buffer. The cells were allowed to bind for 1 h at 4° C. Nonadherent cells were removed by plate inversion for 45 min in cold PBS. The remaining cells were lysed with 5% (vol/vol) Triton X-100 and radioactivity was measured by a Multi Pris γ counter.

Example 6
Incorporation of GPI-B7 into Cell Membranes

Tumor cells were washed three times with PBS/5 mM EDTA. They were then resuspended to $5–10 \times 10^6$ cells per ml and incubated with purified GPI-B7 at 10–40 μg/ml for 2 h at 37° C. with occasional shaking. These cells were washed three times, analyzed by flow cytometry, irradiated, and prepared for costimulation assays.

Example 7
Cell Proliferation Assays

Mononuclear cells (MNC) were isolated from the peripheral blood by 6% dextran sedimentation and Histopaque 1077 (Sigma Chemical Co., St. Louis, Mo.) density centrifugation. The MNC were then prepared for stimulation assays or T-cell separation. T cells were separated by layering MNC over a human T-cell enrichment column (R & D Systems) and collecting the enriched flow-through. T-cell preparations were >92–95% pure with residual contamination of <5–8% $CD16^+$ natural killer (NK) cells as analyzed by flow cytometry.

For polyclonal stimulation, T cells were cultured in complete RPM1 medium 1640 with 10% FBS, supplemented with phorbol 12-myristate 13-acetate (PMA) at 1 ng/ml, at a concentration of $10^5$ cells per well in a 37° C. 5% $CO_2$/95% air incubator. CHO CD16B and CHO GP1-B7 cells were irradiated [8000 rads (80 Gy)], incubated for 30 min at 4° C. with either X63 culture supernatant or purified anti-human or anti-mouse B7 mAb at 5 μg/ml and added to the T cells at a ratio of 8 T cells to 1 CHO cell. The cells were pulsed with [$^3$H]-thymidine (Amersham, Arlington Heights, Ill.) at 1 μCi (37 kBq) per well for the last 6 h of the 3-day incubation.

For allogeneic stimulation by tumor cells, MNC at $2 \times 10^5$ cells per well were cocultured with $5 \times 10^3$ tumor cells, either untreated or treated with GPI-B7 at 40 μg/ml. After 3 days, the mixed lymphocyte tumor reaction (MLTR) cultures were boosted with $5 \times 10^{-1}$ of the same tumor cells, treated or untreated, and incubated for an additional 4 days. The cells were pulsed with [$^3$H]-thymidine at 1 μCi per well for the last 18 h of the incubation.

Example 8
Preparation of Membranes and Incorporation of GPI-B7

EG7 membranes were prepared as described by Meada et al. (1983) *Biochem. Biophys. Acta* 731,115. Cell pellets were homogenized on ice and ultracentrifuged (93,000×g) for 1 hour over a 41% sucrose gradient. The interface was recovered and washed three times. Membranes were resuspended to 100 μg/ml ovalbumin and 10 μg/ml of GPI-anchored B7-1. Two different GPI-B7 chimeric molecules were used. One has the GPI-signal sequence from CD16B (F), the other construct has the GPI-signal sequence from LFA-3 [Staunton et al. (1992) *J. Immunol.* 148, 3271–3274]. The mixture was shaken for 4 hours at 37° C. The membranes were washed again and either analyzed by ELISA or resuspended in HBSS or HBSS containing 2 ng rIL-12, using a 20 g needle, for mice immunizations. For ELISA, the membranes were coated onto microtiter plate wells overnight at 4° C. The wells were blocked with complete RPMI containing 10% FCS and then membranes were analyzed using X63 (negative control), PSRM-3 (anti-human B7-1) or M1/42 (anti-mouse class I). Absorbance or M1/42 binding wells, which was designated as the value 1.0.

Example 9
Immunization of Mice

C57BL/6 mice were immunized with 100 μl total volume intraperitoneally with either HBSS, EG7 membranes (100 μg of equivalent protein) or GPI-B7 incorporated EG7 membranes twice at a 2 week interval. Three weeks after the final immunization, the spleens were harvested and T cell were purified using mouse T cell enrichment columns (R & D Systems). The T cells were used in either MLTR or CTL assays. Some C57BL/6 mice were immunized as described above, except for the addition of IL-12 treatments in vivo. Here, IL-12 (2 ng/mouse) was administered intraperitoneally, beginning one week after first immunization. This treatment was continued every four days for two weeks. Three weeks after the final immunization, spleens were harvested and T cells purified as described.

For tumor challenge experiments, mice were immunized subcutaneously with HBSS, EG7 membranes of GPI-B7 incorporated EG7 membranes, with or without 2 ng IL-12. Two weeks later the mice were boosted. EG7 cells ($10^5$) were injected subcutaneously at a remote site one week after boost. Mice were monitored daily for tumor growth and euthanized when tumors reached 2 cm in diameter.

Example 10
T Cell Assays

For MLTR, T cells purified from immunized mice ($10^5$) were cocultured with EG7 cells ($2 \times 10^4$) for 5 days in a 37°

C. 5% $CO_2$ incubator. T cell proliferation was measured by pulsing the wells with 1 μCi of [$^3$H]-thymidine for the last 18 hours of culture.

For CTL assays, T cells were restimulated in vitro for 5 days with irradiated (15,000 rads) EG7 cells. On the second day of the restimulation 10 U/ml of r IL-2 was added. Live T cells were harvested by density sedimentation using Histopaque 1077 (Sigma) and resuspended to $10^7$ cells/ml. EG7 and autologous lymphocyte Concanavalin A blasts were labeled with 200 μCi of $^{51}$Cr for 2 hours at 37° C. These cells were washed and resuspended to $10^5$ cells/ml. The effectors and targets were mixed at various ratios and a standard 4 hour $^{51}$Cr release assay was performed.

For T cell depletion, T cells, after the restimulation, were pretreated with either 53.6 (anti-CD8) or 145-2C11 (anti-CD3) for 30 minutes. The coated cells were then incubated at 37° C. for 45 minutes with rabbit complement. Live cells were recovered as described above and used in $^{51}$Cr release assay.

In principle, the present invention is also applicable to generation of a cytotoxic immune response against any cell which is detrimental to a human or to an animal, such as a virus-infected cell, a parasite-infected cell or a cell infected with an intracellular microorganism and where that cell does not naturally express the B7-1 surface protein which acts as a costimulatory immune factor. In principle, infected cells can be prepared or cultured by any means known to the art and then the membranes of those cells can be treated with the GPI-anchored B7.1 protein (or other GPI-CoCAm)of the present invention for use in immunotherapy or vaccination. Similarly, cell membranes as part of intact cells which are not themselves infected or cell membranes prepared from such cells can be treated with GPI-anchored B7.1 and with surface marker antigens for infected cells, where those surface marker antigens have been modified to contain a GPI anchor portion in a manner analogous to that taught herein for the creation of the GPI-B7-1 fusion protein. Thus, cells or cell membranes can be prepared for those infection-specific antigens for which sequence information is known, but without any biohazard or difficulty associated with the culture of cells infected with a parasite or pathogenic microorganism or virus. Such artificially produced membranes can be incorporated into vaccine preparations useful for prevention infection or parasitism or into immunotherapeutic compositions for generating a cytotoxic immune response for aiding in clearance of an existing infection with a parasite, microorganism or fungus. A number of marker surface antigens and their coding and/or amino acid sequences are known to the art, and the ordinary skilled artisan can apply the present teachings to the generation of useful therapeutic and/or vaccine compositions.

It is also within the scope of the present invention to create by protein transfer (in vitro) a population of activated CTLs which are specific for targeted tumor cells, cancer cells, pathogen-infected or parasite-infected cells. Those activated CTLs can be introduced into an infected animal or a tumor-bearing animal to aid in the clearance of the infection or parasite or to promote tumor (cancer) regression.

TABLE 1

Protection of C57BL/6 mice from tumor growth by immunization with GPI-B7 incorporated EG7 membranes.

| IMMUNIZED[a] | TUMOR INCIDENCE[b] | |
|---|---|---|
| | −IL-12 | +IL-12 |
| HBSS | 8/10 | 10/10 |
| EG7 membranes | 7/10 | 8/9 |
| EG7 membranes + GPI-B7 | 0/10 | 0/10 |

[a]Mice were immunized as described in the Examples.
[b]Mice were monitored daily for the appearance of subcutaneous tumors. These data are compiled from two independent experiments of 4–5 mice in each experimental group.

We claim:

1. An immunogenic composition comprising:
   a) a tumor cell membrane preparation wherein said tumor cell in nature lacks an immunological costimulatory cell surface molecule (CoCAM), and wherein said tumor cell membrane has been modified by the introduction of a glycosylated phosphatidylinositol (GPI)-anchored B7-1 fusion protein with the result that said tumor cell membrane preparation comprises said glycosylated phosphatidylinositol-anchored B7-1 fusion protein stably incorporated, wherein a DNA molecule encoding the B7-1 portion of the fusion protein is amplified using a human B7-1 clone and primers having the nucleotide sequences provided in SEQ ID NO:1 and SEQ ID NO:2 and wherein a DNA molecule encoding a GPI anchor signal portion is amplified using a human CD16B cDNA clone and primers having the nucleotide sequences provided in SEQ ID NO:3 and SEQ ID NO:4 and wherein the DNA molecules were annealed using a polymerase chain amplification reaction and primers having the nucleotide sequences provided in SEQ ID NO:1 and SEQ ID NO:4;
   b) a pharmaceutically acceptable carrier; and
   c) at least one cytokine in an amount effective for augmenting an immune response.

2. The immunogenic compostion of claim 1 wherein the cytokine is interleukin-6 or interleukin-12.

3. The immunogenic composition of claim 1 further comprising an immunological adjuvant.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "Oligonucleotide."

(iii) HYPOTHETICAL: NO (xi) SEQUENCE DESCRIPTION: SEQ ID NO:1:

CCCTAAGCTT CTGAAGCCAT GGGC    24

(2) INFORMATION FOR SEQ ID NO:2:

```
    (i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide."

(iii) HYPOTHETICAL: NO (xi) SEQUENCE DESCRIPTION: SEQ ID NO:2:

CAATTGATCA GGAAAATGCT CTTGCTT                                        27

(2) INFORMATION FOR SEQ ID NO:3:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide."

(iii) HYPOTHETICAL: NO (xi) SEQUENCE DESCRIPTION: SEQ ID NO:3:

CCTGATCAAT TGGCAGTGTC AACCATCTCA                                     30

(2) INFORMATION FOR SEQ ID NO:4:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide."

(iii) HYPOTHETICAL: NO (xi) SEQUENCE DESCRIPTION: SEQ ID NO:4:

TCTTCTAGAG CTTCAAATGT TTGTCTTCAC AGA                                 33
```